United States Patent
van Beek et al.

(10) Patent No.: US 11,896,557 B2
(45) Date of Patent: Feb. 13, 2024

(54) DOCKING STATION AND METHOD FOR LOADING A MEDICINE TRANSPORT PLATE

(71) Applicant: VMI Holland B.V., Epe (NL)

(72) Inventors: Johan Gerard van Beek, Epe (NL); Anthonius Maria Hendrina de Boer, Epe (NL); Cornelis Jan Jochemsen, Epe (NL); Patrick van Voorn, Epe (NL)

(73) Assignee: VMI Holland B.V., Epe (NL)

( * ) Notice: Subject to any disclaimer, the term of this patent is extended or adjusted under 35 U.S.C. 154(b) by 0 days.

(21) Appl. No.: 17/690,021

(22) Filed: Mar. 9, 2022

(65) Prior Publication Data

US 2022/0192926 A1    Jun. 23, 2022

Related U.S. Application Data

(63) Continuation of application No. PCT/EP2021/061573, filed on May 3, 2021.

(51) Int. Cl.
*A61J 7/00*   (2006.01)
*B65G 1/08*   (2006.01)
*G16H 20/13*  (2018.01)

(52) U.S. Cl.
CPC .............. *A61J 7/0084* (2013.01); *B65G 1/08* (2013.01); *G16H 20/13* (2018.01); *B65G 2203/0283* (2013.01)

(58) Field of Classification Search
CPC ..... G07F 17/0092; A47J 7/0069; G16H 20/13
See application file for complete search history.

(56) References Cited

U.S. PATENT DOCUMENTS

| | | |
|---|---|---|
| 4,047,620 A | 9/1977 | Deininger |
| 8,380,346 B2 | 2/2013 | Chudy et al. |
| 9,002,510 B2 | 4/2015 | Chudy et al. |
| 9,355,221 B2 | 5/2016 | Chudy et al. |
| 9,355,222 B2 | 5/2016 | Chudy et al. |
| 9,672,327 B2 | 6/2017 | Chudy et al. |
| 10,650,921 B2 | 5/2020 | Chudy et al. |
| 2003/0057231 A1 | 3/2003 | Kim |
| 2004/0074916 A1 | 4/2004 | Priebe |
| 2009/0044489 A1* | 2/2009 | Siegel ............ B65B 5/103 53/247 |

(Continued)

FOREIGN PATENT DOCUMENTS

| | | |
|---|---|---|
| EP | 2093722 B1 | 5/2013 |
| EP | 2786938 A1 | 10/2014 |
| WO | 2020/071905 A2 | 4/2020 |

*Primary Examiner* — Timothy R Waggoner
(74) *Attorney, Agent, or Firm* — N.V. Nederlandsch Octrooibureau

(57) ABSTRACT

A method for loading a medicine transport plate with one or more medicine items using a docking station includes the steps of moving a preparation release mechanism of a docking station into a preparation holding state; inserting the one or more medicine items into one or more preparation compartments in the docking station; loading the medicine transport plate into the docking station; and moving the preparation release mechanism from the preparation holding state into a preparation release state to release the one or more medicine items from the preparation compartments.

26 Claims, 16 Drawing Sheets

(56) References Cited

U.S. PATENT DOCUMENTS

| | | | |
|---|---|---|---|
| 2009/0152291 A1* | 6/2009 | Ohmura | G07F 17/0092 221/197 |
| 2009/0188937 A1* | 7/2009 | Kim | A61J 7/0069 221/312 B |
| 2013/0018503 A1* | 1/2013 | Carson | B65D 75/327 700/216 |
| 2014/0261881 A1* | 9/2014 | Chudy | A61J 7/0084 141/94 |
| 2017/0217619 A1* | 8/2017 | Hellenbrand | B65B 35/30 |
| 2019/0080790 A1 | 3/2019 | Patel | |
| 2020/0391887 A1* | 12/2020 | Takada | A61J 7/04 |
| 2020/0402632 A1* | 12/2020 | van Schelven | G06Q 10/30 |

\* cited by examiner

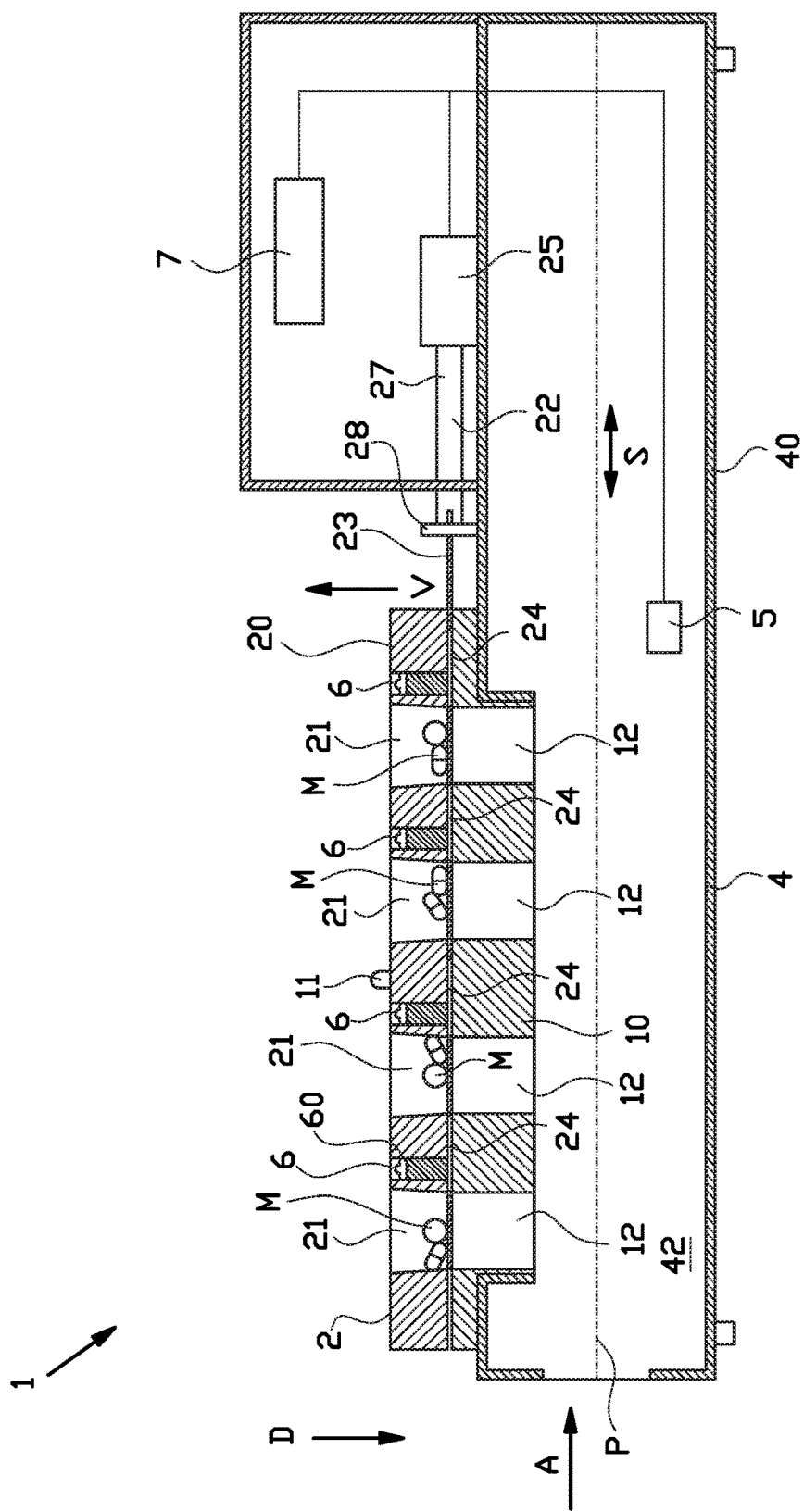

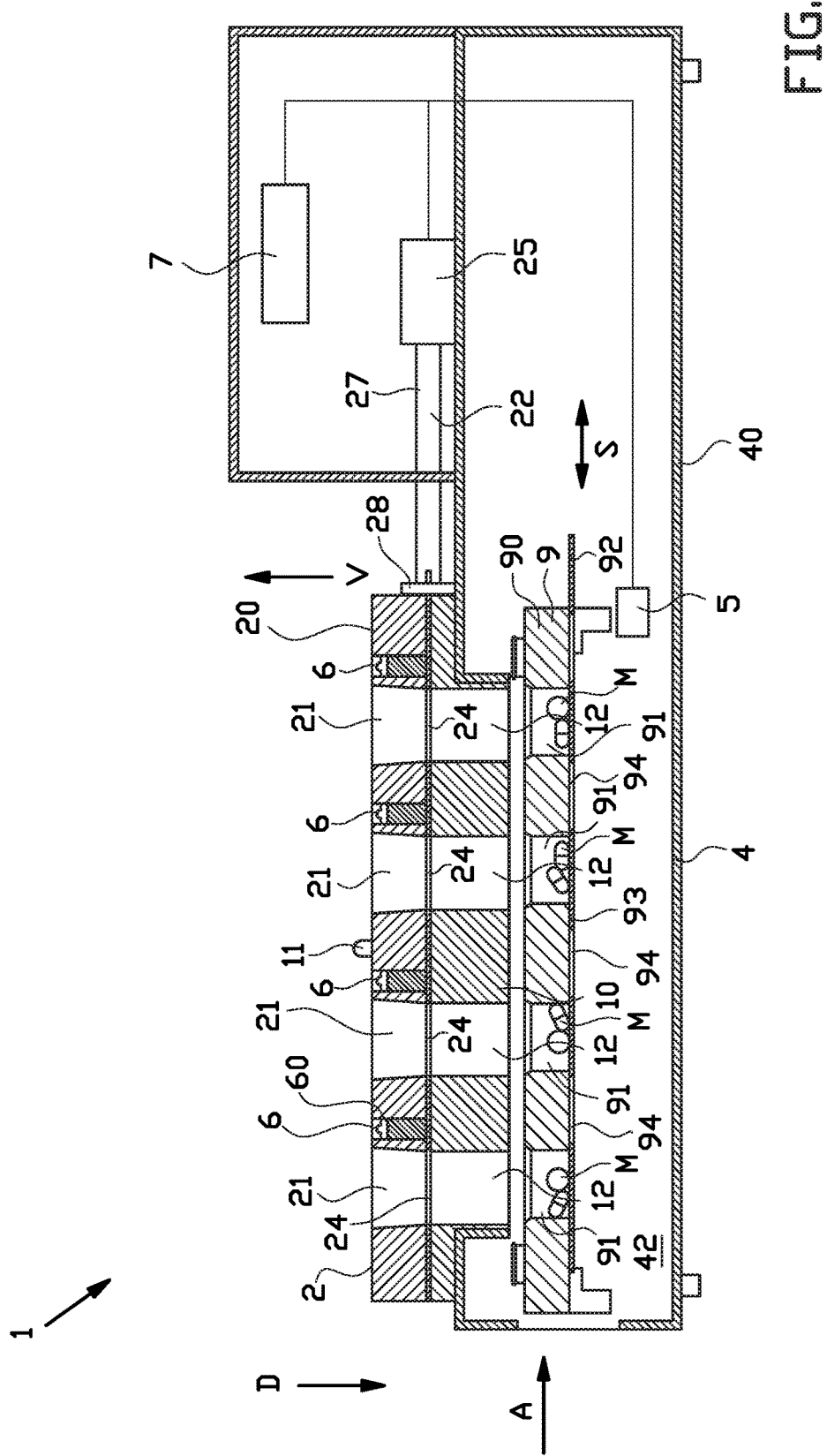

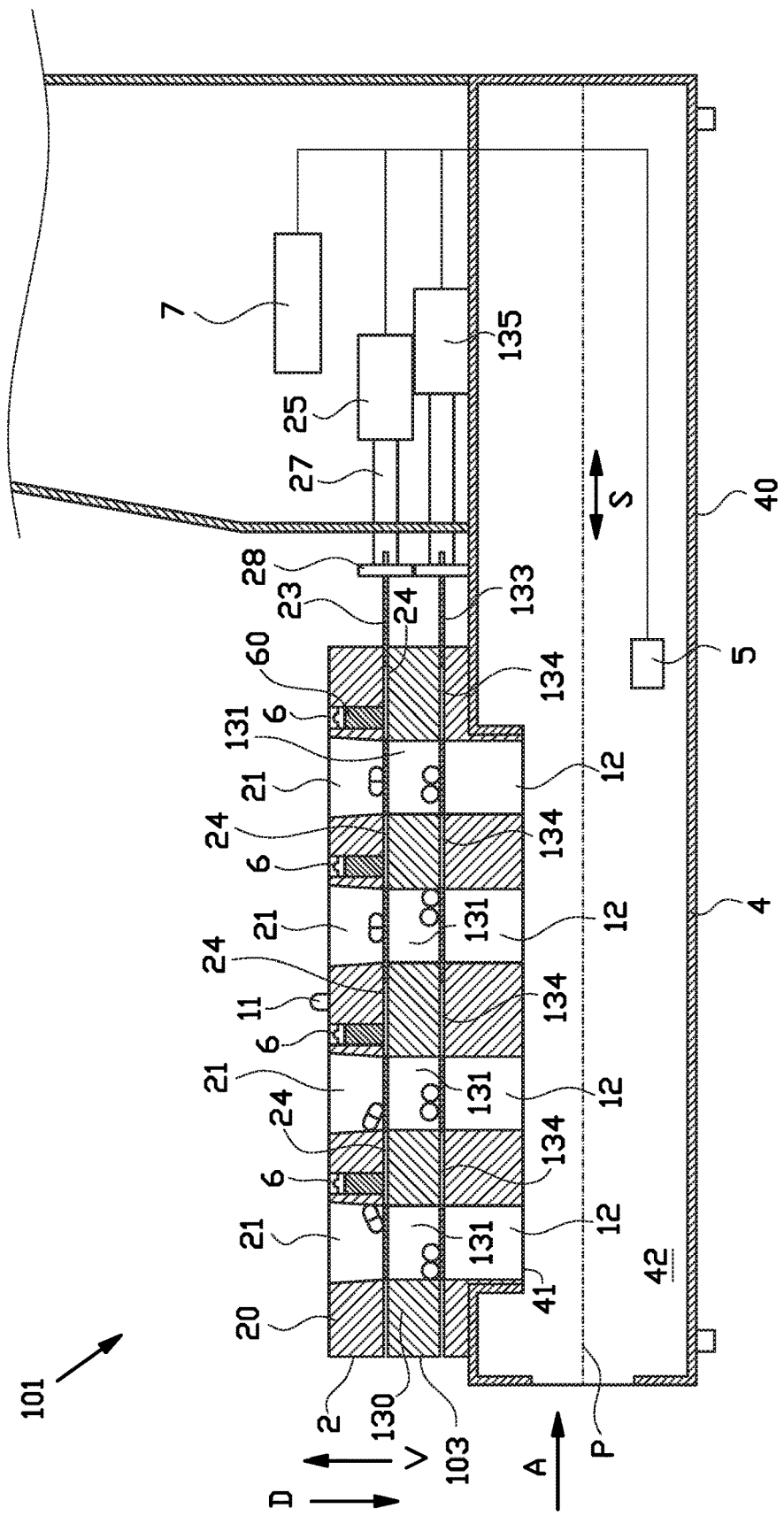

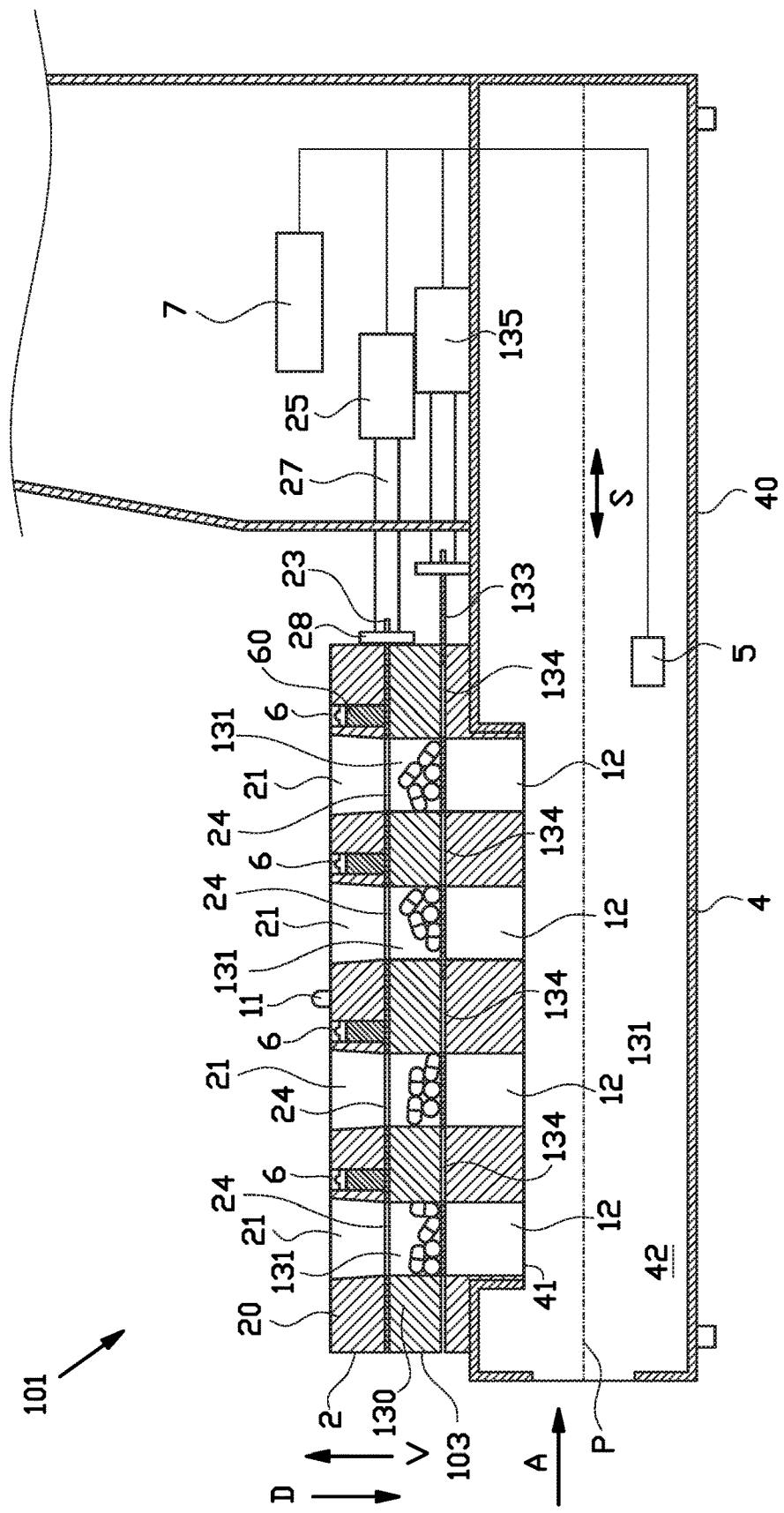

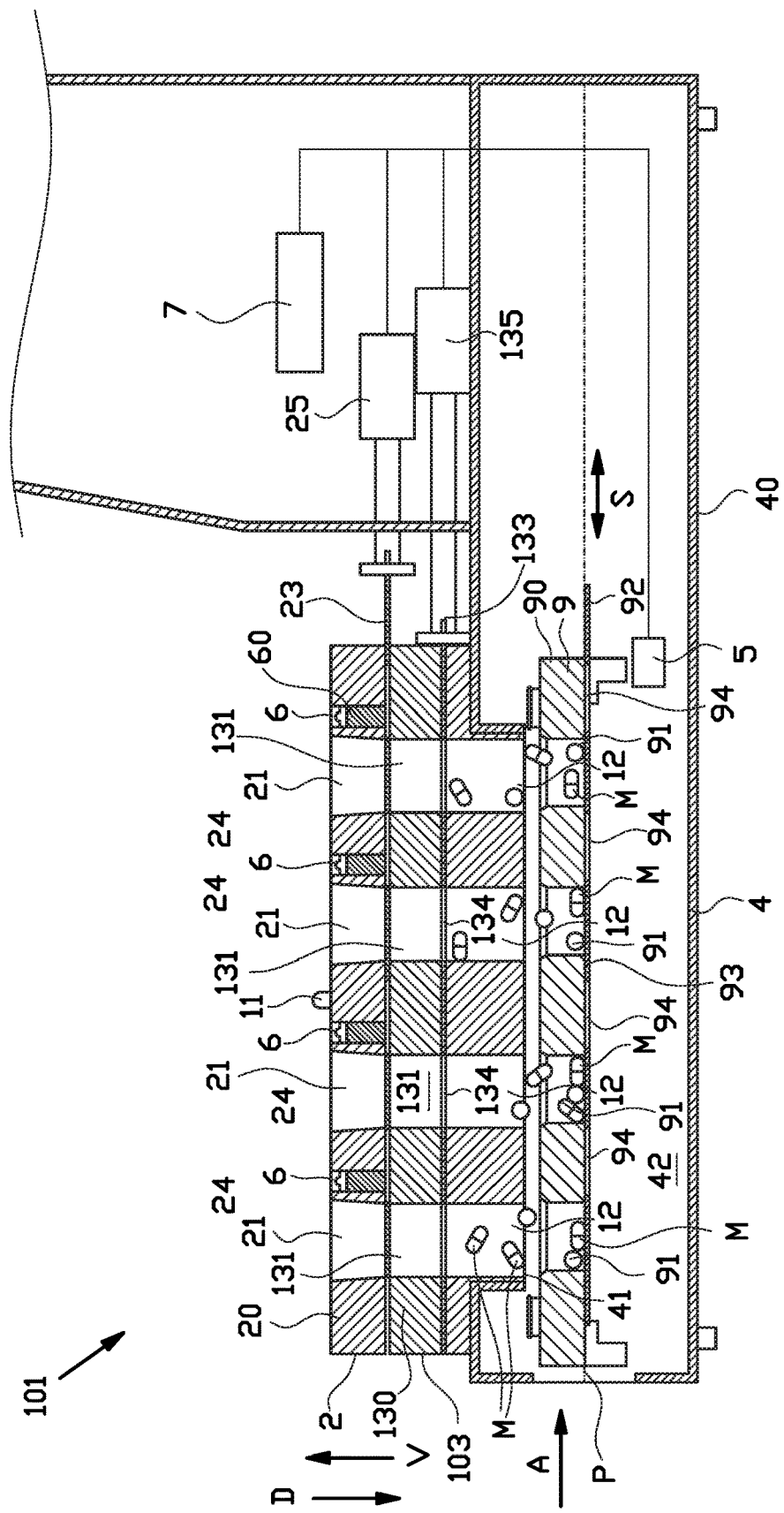

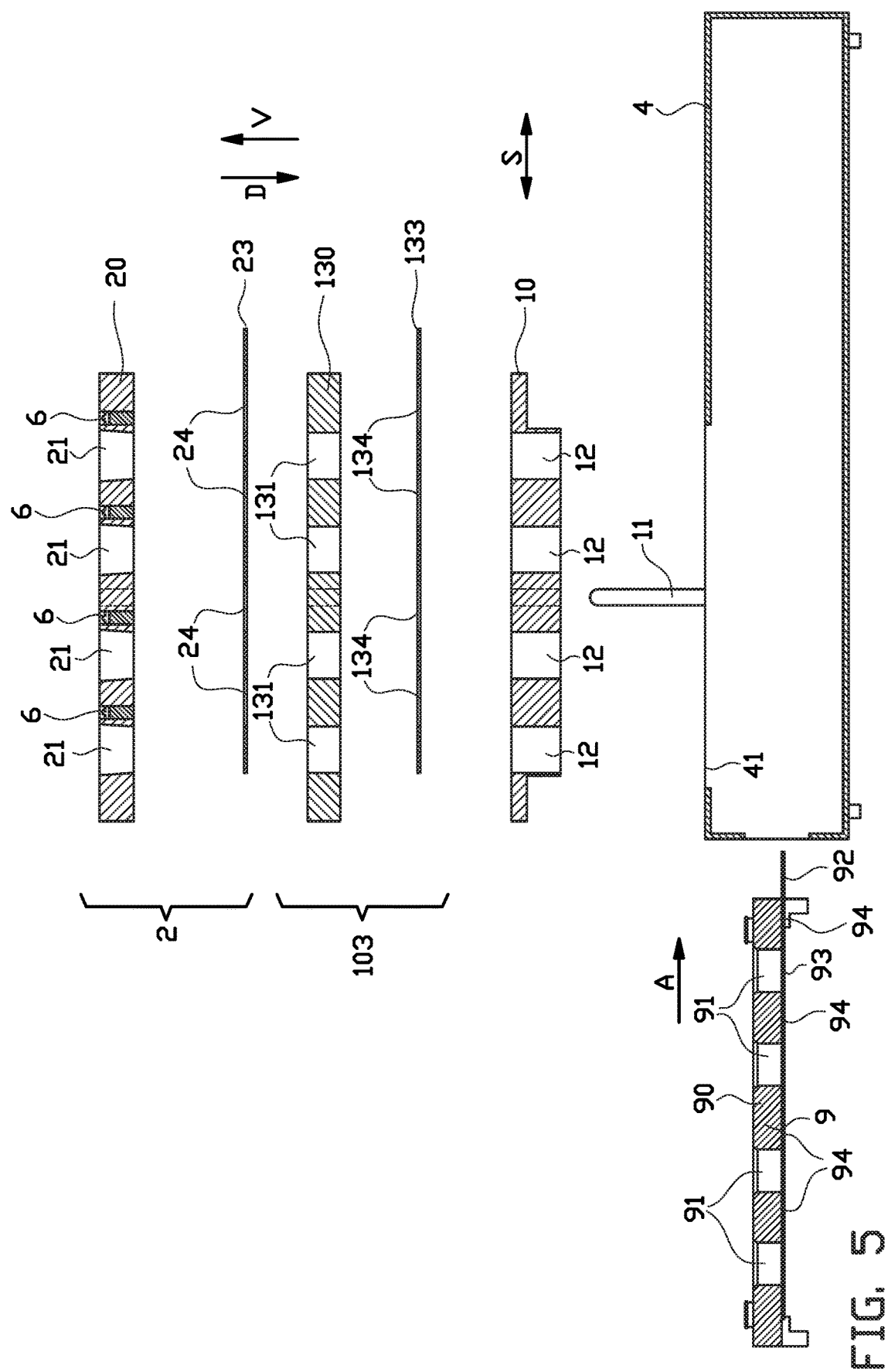

DOCKING STATION AND METHOD FOR LOADING A MEDICINE TRANSPORT PLATE

BACKGROUND

The invention relates to a docking station and a method for loading a medicine transport plate.

EP 2 791 012 B1 discloses a device for automatically dispensing pills, tablets or capsules, in particular for medical use. It is known to use such automated dispensing devices to handle fast-moving medicaments, i.e. medicaments that are frequently prescribed. The known device comprises a plurality of feeder units with canisters that hold a specific type of medicament in bulk. Such canisters are not suitable for storing slower moving medicaments, i.e. medicaments that are prescribed infrequently, or medicaments with an odd shape or packaging. EP 2 791 012 B1 further discloses a supply unit with a tray for separately supplying a selection of medicaments to the automated dispensing device.

EP 2 093 722 B1 discloses a docking station to which a tray-like holder is docked. The tray-like holder is loaded in the docking station with a range of medicaments. The tray-like holder is provided with a plurality of cells for receiving the medicaments from the docking station. The tray-like holder further comprises a gate that is movable between a first position in which the cell outlets are closed and a second position which the cell outlets are open to discharge the medicaments from the cell. The gate of the tray like holder remains in the first position during loading in the docking station and transport to the automated dispensing device. When the tray-like holder is arrives at the automated dispensing device, the loaded range of medicaments can be dispensed together with the medicaments that are stored in bulk in the automated dispensing device by moving the gate into the second position.

EP 2 093 722 B1 discloses two embodiments which feature indicators that indicate the cell of the tray-like holder into which medicaments are to be received. In one embodiment the indicators are provided on the holder and electrical contacts are provided between the holder and the docking station to allow for communication between a controller in the docking station and the indicators on the tray-like holder. In the other embodiment, the docking station is provided with a guide that is associated with the docking station and that extends over the tray-like holder as a sort of overlay. The guide is provided with a plurality of openings arranged in a pattern identical to the cells in the tray-like holder. The guide is further provided with a plurality of indicators positioned on the guide next to each cell of the tray-like holder to provide visible information viewable next to the corresponding cell when the holder is docked at the docking station.

SUMMARY OF THE INVENTION

A disadvantage of the docking station of EP 2 093 722 B1 is that the tray-like holder needs to be docked to the docking station to start the filling process. In the embodiment with the indicators on the tray-like holder, communication needs to be established between the indicators and the controller of the docking station. In the embodiment with the guide, the tray-like holder needs to be positioned below the openings of the guide to receive the medicaments directly through said guide. As the tray-like holder also needs to be cleaned regularly, valuable time is lost as it merely sits in the docking station waiting to be filled. Moreover, the number of tray-like holders in the dispensing process as a whole may be limited.

It is an object of the present invention to provide a docking station and a method for loading a medicine transport plate, wherein the medicine transport plate can be loaded more efficiently.

According to a first aspect, the invention provides a docking station for loading a medicine transport plate with one or more medicine items, wherein the medicine transport plate comprises a plurality of storage compartments for receiving the one or more medicine items from the docking station, wherein the docking station comprises a preparation section for manually preparing the one or more medicine items for loading and a transport plate section in a drop direction below the preparation section for holding the medicine transport plate in a transport plate plane, wherein the preparation section comprises a plurality of preparation compartments for receiving the one or more medicine items prior to loading the medicine transport plate and a preparation release mechanism that is movable between a preparation holding state for holding the one or more medicine items in the plurality of preparation compartments and a preparation release state for releasing the one or more medicine items from the plurality of preparation compartments in the drop direction.

Hence, the medicine items can already be prepared in the preparation section, even when the medicine transport plate is absent from the transport plate section. Moreover, the medicine items remain easily visible in the preparation compartments, i.e. near the upper surface of the docking station, until they are released through the preparation release mechanism. The medicine transport plate only needs to be present in the transport plate section for a relatively short period of time when the medicine items are released into said transport plate section. Hence, less medicine transport plates are required to supply the automated medicine dispenser. Also, more time is available for cleaning of the medicine transport plates. Moreover, the medicine transport plate can be 'out of sight' in the transport plate section for a shorter period of time, thereby preventing the chance of human error as a result of a loss of concentration and/or an unexpected interruption. Consequently, there is a reduced risk of loading the wrong medicine transport plate or loading the same medicine transport plate twice.

In a preferred embodiment the preparation release mechanism is arranged for releasing the one or more medicine items from all preparation compartments of the plurality of preparation compartments simultaneously. In this way, the preparation release mechanism can be simplified significantly.

In a further embodiment the preparation release mechanism comprises a preparation release plate with a plurality of preparation release openings, wherein the preparation release plate is movable in a sliding direction parallel to the transport plate plane between a preparation holding position in which the plurality of preparation release openings are out of line with the plurality of preparation compartments and a preparation release position in which the plurality of preparation release openings are registered with the plurality of preparation compartments in the drop direction. Hence, in the preparation holding position, the preparation release plate effectively closes the preparation compartments in the drop direction, whereas in the preparation release position the one or more medicine items in the preparation compartments can freely drop through the preparation release openings in the drop direction.

In another embodiment the docking station comprises one or more sensors for detecting presence or absence of the medicine transport plate in the transport plate section. The one or more sensors may for example detect the passage of the medicine transport plate beyond a certain reference point and/or the arrival of the medicine transport plate in the intended transport plate position within the transport plate section. By detecting the presence or absence of the medicine transport plate in the transport plate section, it can be prevented that the one or more medicine items are released into the transport plate section prematurely, i.e. prior to the correct placement of the medicine transport plate in said transport plate section.

Preferably, the docking station comprises a preparation release actuator for driving the movement of the preparation release mechanism from the preparation holding state to the preparation release state, wherein the docking station further comprises a control unit that is operationally connected to the one or more sensors and the preparation release actuator, wherein the control unit is configured for controlling the preparation release actuator to maintain the preparation release mechanism in the preparation holding state as long as the control unit receives a signal from the one or more sensors indicative of the absence of the medicine transport plate in the transport plate section. By actively controlling preparation release actuator, the state of the preparation release mechanism can be controlled reliably and/or automatically. It is noted that a 'signal indicative of the absence of the medicine transport plate' in this embodiments and any embodiments hereafter can be an electronic signal or the absence of such an electronic signal from the one or more sensors, depending on how the control unit is configured to interpret the electronic signals, or absence thereof, from the one or more sensors.

Alternatively, the docking station comprises a preparation blocking member for blocking the movement of the preparation release mechanism from the preparation holding state to the preparation release state, wherein the docking station further comprises a control unit that is operationally connected to the one or more sensors and the preparation blocking member, wherein the control unit is configured for controlling the preparation blocking member to block the preparation release mechanism in the preparation holding state as long as the control unit receives a signal from the one or more sensors indicative of the absence of the medicine transport plate in the transport plate section. Hence, as long as the preparation blocking member blocks the preparation release mechanism, said preparation release mechanism can not be moved from the preparation holding state to the preparation release state, neither manually nor automatically.

In one embodiment the preparation release mechanism is arranged to operate automatically in response to the insertion of the medicine transport plate. Hence, after preparing the medicine items manually in the preparation section, no further human interaction is required other than inserting the medicine transport plate in the docking station. The loading of the medicine transport plate can be performed fully automatically, i.e. without human intervention.

Alternatively, the preparation release mechanism is arranged to be operated semi-automatically via a user-interface which allows for initiation of the operation of the preparation release mechanism only when one or more predetermined checks have been completed. Examples of such checks could include, but are not limited to: the detection of the presence of the medicine transport plate in the slot, the reading of the information of an RFID tag, and/or a digital visual inspection of the prepared medicine items.

Alternatively, the preparation release mechanism is manually operable. Hence, no actuator is needed to operate the preparation release mechanism.

In another embodiment the preparation section comprises a preparation body, wherein the plurality of preparation compartments are formed in said preparation body, wherein the docking station further comprises a base for supporting the preparation body in a stacking direction perpendicular to the transport plate plane and one or more positioning members for positioning the preparation body on the base in a direction parallel to the transport plate plane, wherein the preparation body is removable from the base in the stacking direction. After removing the preparation body from the base, the preparation section and the base can be cleaned more easily.

In another embodiment the docking station comprises a buffer section in the drop direction between the preparation section and the transport plate section, wherein the buffer section comprises a plurality of buffer compartments for receiving the one or more medicine items from the preparation section prior to loading the medicine transport plate and a buffer release mechanism that is movable between a buffer holding state for holding the one or more medicine items in the plurality of buffer compartments and a buffer release state for releasing the one or more medicine items from the plurality of buffer compartments in the drop direction. The one or more medicine items can be prepared in the preparation section in several batches, wherein each batch can be released from the preparation compartments into the buffer compartments located below said preparation compartments in the drop direction prior to preparing the next batch. The one or more medicine items can be collected and/or buffered in the buffer compartments until all medicine items from all of the batches have been prepared and buffered in the buffer compartments. The buffer release mechanism can subsequently be moved into the buffer release state to release all medicine items collected in one or more of the buffer compartments during the transfer of said batches from the preparation section to the buffer section.

Preferably, the buffer release mechanism is arranged for releasing the one or more medicine items from all buffer compartments of the plurality of buffer compartments simultaneously. In this way, the buffer release mechanism can be simplified significantly.

In a further embodiment the buffer release mechanism comprises a buffer release plate with a plurality of buffer release openings, wherein the buffer release plate is movable in a sliding direction parallel to the transport plate plane between a buffer holding position in which the plurality of buffer release openings are out of line with the plurality of buffer compartments and a buffer release position in which the plurality of buffer release openings are registered with the plurality of buffer compartments in the drop direction. Hence, in the buffer holding position, the buffer release plate effectively closes the buffer compartments in the drop direction, whereas in the buffer release position the one or more medicine items in the buffer compartments can freely drop through the buffer release openings in the drop direction.

In a further embodiment the docking station comprises one or more sensors for detecting presence or absence of the medicine transport plate in the transport plate section and a buffer release actuator for driving the movement of the buffer release mechanism from the buffer holding state to the buffer release state, wherein the docking station further comprises a control unit that is operationally connected to the one or more sensors and the buffer release actuator, wherein the control unit is configured for controlling the buffer release actuator to maintain the buffer release mechanism in the buffer holding state as long as the control unit receives a signal from the one or more sensors indicative of the absence of the medicine transport plate in the transport plate section.

Alternatively, the docking station comprises one or more sensors for detecting presence or absence of the medicine transport plate in the transport plate section and a buffer blocking member for blocking the movement of the buffer release mechanism from the buffer holding state to the buffer release state, wherein the docking station further comprises a control unit that is operationally connected to the one or more sensors and the buffer blocking member, wherein the control unit is configured for controlling the buffer blocking member to block the buffer release mechanism in the buffer holding state as long as the control unit receives a signal from the one or more sensors indicative of the absence of the medicine transport plate in the transport plate section. In the two embodiments discussed above the buffer release mechanism can take over the holding functionality from the preparation release mechanism in the same way as previously described for said preparation release mechanism. Hence, the preparation release mechanism can be operated independently of the buffer release mechanism to transfer one or more batches of medicine items from the preparation section into the buffer section, while the buffer section buffers said transferred batches of medicine items until the medicine transport plate is present in the transport plate section to receive the buffered batches of medicine items.

In further embodiment the plurality of preparation compartments are wider than the plurality of buffer compartments in at least one direction perpendicular to the drop direction. Hence, the medicine items can remain easily visible in the preparation compartments, i.e. near the upper surface of the docking station, until they are released through the preparation release mechanism into the buffer section below.

In further embodiment the preparation section and the buffer section comprise a preparation body and a buffer body, respectively, wherein the plurality of preparation compartments and the plurality of buffer compartments are formed in said preparation body and said buffer body, respectively, wherein the docking station further comprises a base for supporting the preparation body and the buffer body in a stacking direction perpendicular to the transport plate plane and one or more positioning members for positioning the preparation body and the buffer body on the base in a direction parallel to the transport plate plane, wherein the preparation body and the buffer body are removable from the base in the stacking direction. After removing the preparation body and the buffer body from the base, the preparation section, the buffer section and the base can be cleaned more easily.

In another embodiment the docking station further comprises a plurality of controllable indicators for selectively indicating one or more preparation compartments of the plurality of preparation compartments. The indicators can be used as an aid for manually loading the one or more medicine items into the correct preparation compartments. The indicators may have different states, i.e. for indicating the number of medicine items to be inserted or the type of medicine items to be inserted in the preparation compartments of the preparation section. Each indicator is associated with and/or viewable next to a respective preparation compartments of the plurality of preparation compartments.

Preferably, the docking station comprises one or more sensors for detecting presence or absence of the medicine transport plate in the transport plate section and a control unit that is operationally connected to the one or more sensors and the plurality of indicators, wherein the control unit is configured for disabling the plurality of indicators when the control unit receives a signal from the one or more sensors indicative of the presence of the medicine transport plate in the transport plate section. Hence, the preparation of the one or more medicine items can only be performed with the aid of the plurality of indicators when the medicine transport plate is not present in the transport plate section. This forces the operator to first complete the manual preparation of the one or more medicine items in the preparation section prior to insertion of the medicine transport plate in the transport plate section. Consequently, the medicine transport plate is present in the transport plate section for a limited period of time only, thereby preventing the chance of human error as a result of a loss of concentration and/or an unexpected interruption. Consequently, there is a reduced risk of loading the wrong medicine transport plate or loading the same medicine transport plate twice.

Preferably, the plurality of indicators are visual indicators. The indicators may thus conveniently visually indicate which of the preparation compartments are ready to receive a medicine item of a certain type, i.e. with an 'on' or 'off' light. The indicators may further shown different colour codes or patterns to indicate the number or type of medicine items to be inserted.

In another embodiment the transport plate section comprises a housing that defines a slot extending in the transport plate plane for holding the medicine transport plate in said transport plate plane within the housing. The slot can at least partially accommodate the medicine transport plate and prevent that dust and/or other contaminants are collected in the medicine transport plate during its time in the docking station.

Preferably, the slot is open in a docking direction parallel to the transport plate plane for slidably receiving the medicine transport plate into said slot. By sliding the medicine transport plate into and out of the slot through the transport plate plane, the height of the docking station can be kept relatively low.

In a further embodiment the transport plate section further comprises a transport plate locking member for locking the medicine transport plate in the slot when the medicine transport plate is correctly received in said slot. The transport plate locking member can prevent that the medicine transport plate unintentionally shifts position during the transfer of the one or more medicine items into the medicine transport plate in the drop direction.

In a further embodiment the transport plate section further comprises a transport plate blocking member for preventing insertion of the medicine transport plate into the slot. By preventing the insertion of the medicine transport plate into the slot except for the moment that all of the medicine items are prepared and ready for transfer to the medicine transport plate, the medicine transport plate can be 'out of sight' in the transport plate section for a shorter period of time, thereby preventing the chance of human error as a result of a loss of concentration and/or an unexpected interruption. Consequently, there is a reduced risk of loading the wrong medicine transport plate or loading the same medicine transport plate twice.

According to a second aspect, the invention provides a method for loading a medicine transport plate with one or more medicine items with the use of the docking station according to any of the preceding claims, wherein the method comprises the steps of: moving the preparation release mechanism into the preparation holding state; manually inserting and holding the one or more medicine items in the plurality of preparation compartments prior to loading the medicine transport plate; and moving the preparation release mechanism from the preparation holding state into the preparation release state to release the one or more medicine items from the plurality of preparation compartments in the drop direction.

The method relates the practical implementation of the docking station and therefore has the same technical advantages, which will not be repeated hereafter.

In a preferred embodiment of the method the one or more medicine items are released from all preparation compartments of the plurality of preparation compartments simultaneously.

In a further embodiment of the method the preparation release mechanism is maintained in the preparation holding state as long as the medicine transport plate is absent in the transport plate section.

In one embodiment the preparation release mechanism is operated automatically in response to the insertion of the medicine transport plate.

Alternatively, the preparation release mechanism is operated semi-automatically via a user-interface which allows for initiation of the operation of the preparation release mechanism only when one or more predetermined checks have been completed.

Alternatively, the preparation release mechanism is manually operated.

In a further embodiment of the method the docking station comprises a buffer section in the drop direction between the preparation section and the transport plate section, wherein the buffer section comprises a plurality of buffer compartments for receiving the one or more medicine items from the preparation section prior to loading the medicine transport plate and a buffer release mechanism that is movable between a buffer holding state for holding the one or more medicine items in the plurality of buffer compartments and a preparation release state for releasing the one or more medicine items from the plurality of buffer compartments in the drop direction, wherein the method further comprises the steps of: moving the buffer release mechanism into the buffer holding state; receiving the one or more medicine items from the preparation section and holding said one or more medicine items in the plurality of buffer compartments prior to loading the medicine transport plate; and moving the buffer release mechanism from the buffer holding state into the buffer release state to release the one or more medicine items from the plurality of buffer compartments in the drop direction.

Preferably, the one or more medicine items are released from all buffer compartments of the plurality of buffer compartments simultaneously.

In a further embodiment the buffer release mechanism is maintained in the buffer holding state as long as the medicine transport plate is absent in the transport plate section.

In a further embodiment the docking station further comprises a plurality of controllable indicators for selectively indicating one or more preparation compartments of the plurality of preparation compartments, wherein the method further comprises the step of disabling the plurality of indicators when the medicine transport plate is present in the transport plate section.

In another embodiment of the method the docking station comprises a housing that defines a slot extending in the transport plate plane for holding the medicine transport plate in said transport plate plane within the housing, wherein the method further comprises the step of locking the medicine transport plate in the slot when the medicine transport plate is correctly received in said slot.

In another embodiment of the method the docking station comprises a housing that defines a slot extending in the transport plate plane for holding the medicine transport plate in said transport plate plane within the housing, wherein the method further comprises the step of blocking insertion of the medicine transport plate into the slot until all of the medicine items that are to be loaded in the medicine transport plate have been received in the docking station and are ready to be released from said docking station into the medicine transport plate.

The various aspects and features described and shown in the specification can be applied, individually, wherever possible. These individual aspects, in particular the aspects and features described in the attached dependent claims, can be made subject of divisional patent applications.

BRIEF DESCRIPTION OF THE DRAWINGS

The invention will be elucidated on the basis of an exemplary embodiment shown in the attached drawings, in which:

FIG. 3A shows a cross section of the docking station according to the line III-III in FIG. 1 during a first step of loading the medicine transport plate;

FIG. 3B shows a cross section of the docking station according to FIG. 3A during a subsequent step of loading the medicine transport plate;

FIG. 4A shows a cross section of the alternative docking station according to the line IV-IV in FIG. 2 during a first step of loading the medicine transport plate;

FIGS. 4B and 4C show cross sections of the alternative docking station according to FIG. 4A during subsequent steps of loading the medicine transport plate;

FIG. 5 shows an exploded view of the docking station according to FIG. 4A;

DETAILED DESCRIPTION OF THE INVENTION

Figure 1:
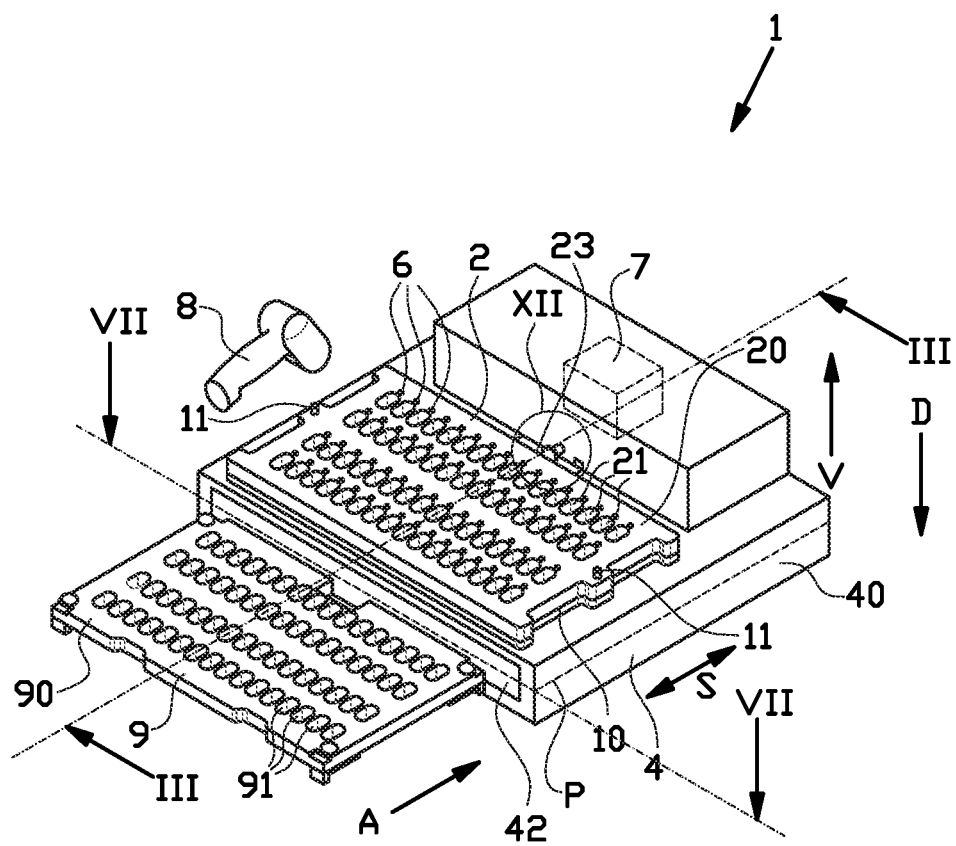
FIG. 1 shows an isometric view of a docking station and a medicine transport plate according to a first exemplary embodiment of the invention.
Figure 2:
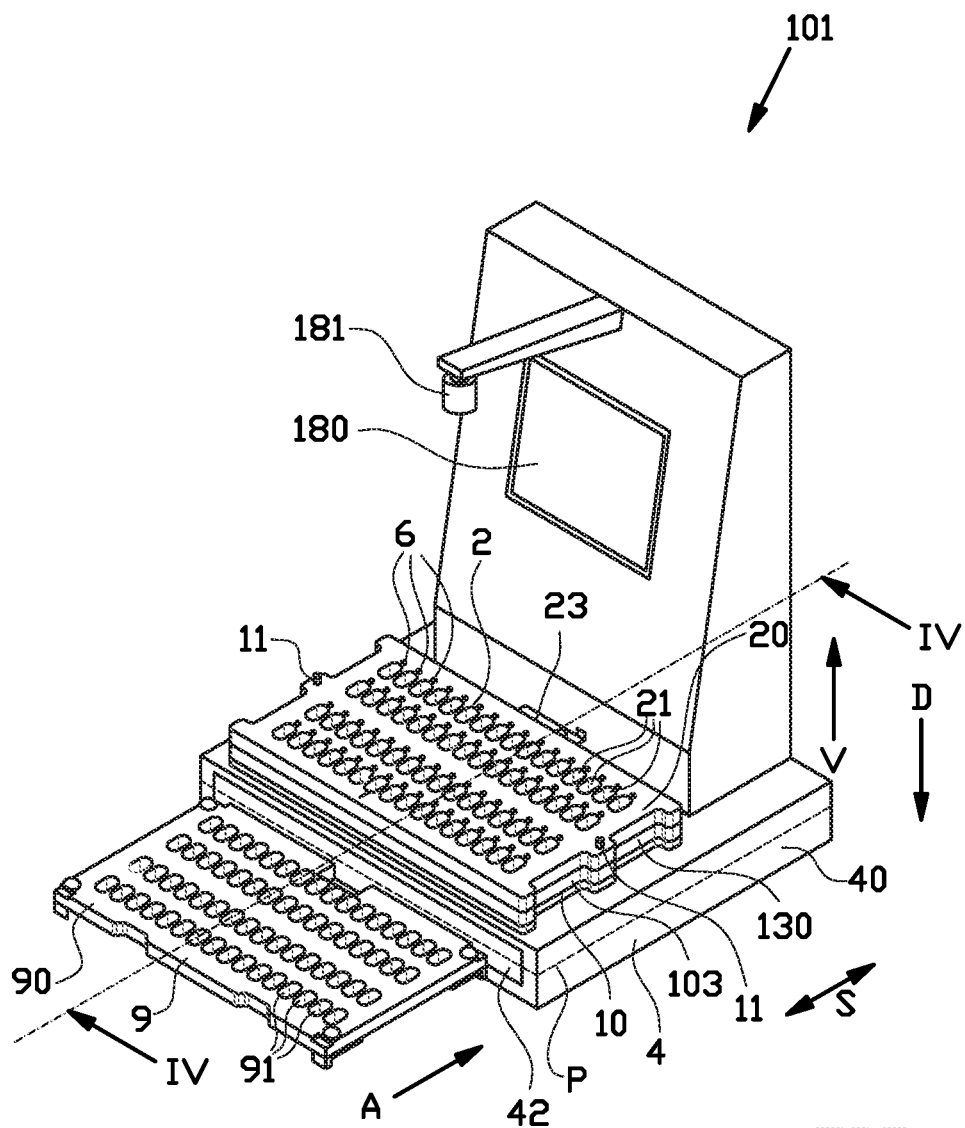
FIG. 2 shows an isometric view of an alternative docking station and a medicine transport plate according to a second exemplary embodiment of the invention.

FIGS. 1, 3A, 3B and 7 show a docking station 1 according to an exemplary first embodiment of the invention, for filling or loading a medicine transport tray or medicine transport plate 9 with one or more medicaments or medicine articles or items M, such as tablets, pills or blister packaging including one or more of said medicine items M.

The medicine transport plate 9 may be a conventional medicine transport plate, for example like the one disclosed in WO 2020/071905 A1. The medicine transport plate 9 comprises a plate-like or transport plate body 90 and a plurality of storage cells or storage compartments 91 formed through said transport plate body 90 in a release direction, a discharge direction or a drop direction D for receiving the one or more medicine items M from the docking station 1. The drop direction D is vertical or substantially vertical. The plurality of storage compartments 91 are arranged in a pattern, in particular in a grid and/or in a plurality of rows and columns.

As best seen in FIG. 3B, the medicine transport plate 9 further comprises a transport plate release mechanism 92 for releasing the one or medicine items M from the storage compartments 91 in the drop direction D, i.e. when the medicine transport plate 9 is slotted into an automated dispensing device similar to the one disclosed in EP 2 791 012 B1. In this exemplary embodiment, the transport plate release mechanism 92 comprises a tray release gate or transport plate release plate 93 that is slidable with respect to the transport plate body 90 and that comprises a plurality of tray release openings 94 that are arranged to be out of line with the plurality of storage compartments 91 in one sliding position of the transport plate release plate 93 and registered or aligned with the plurality of storage compartments 91 in another sliding position of the transport plate release plate 94 in a manner known per se.

As shown in FIGS. 1, 3A and 3B, the docking station 1 comprises a preparation section 2 for manually preparing the one or medicine items M for loading prior to actually loading said one or more medicine items M in the medicine transport plate 9. The docking station 1 further comprises a transport plate section 4 in the drop direction D below or underneath the preparation section 2 for holding the medicine transport plate 9 in a transport plate plane P. In this exemplary embodiment, the transport plate plane P is horizontal or substantially horizontal and/or perpendicular or substantially perpendicular to the drop direction D. In other words, the transport plate section 4 is arranged for receiving the medicine transport plate 9 in a horizontal or substantially horizontal orientation. The drop direction D is perpendicular or substantially perpendicular the transport plate plane P. The transport plate plane P is located in the drop direction D below or vertically below the preparation section 2.

As best seen in FIG. 1, the preparation section 2 comprises a preparation body 20 and a plurality of preparation cells or preparation compartments 21 formed through said preparation body 20 in the drop direction D for receiving the one or more medicine items M prior to loading the medicine transport plate 9. The preparation compartments 21 are arranged in the same pattern as the storage compartments 91 in the medicine transport plate 9. Each preparation compartment 21 extends completely through the preparation body 20 in the drop direction D, i.e. as a through-hole or a chute. In this example, the preparation compartments 21 narrow in the drop direction D. In other words, the preparation compartments 21 slightly taper in the drop direction D. As such, the opening at the top of the preparation compartment 21 is slightly wider than the opening at the bottom of the preparation compartment 21.

As best seen in FIGS. 3A and 3B, the preparation section 2 further comprises a preparation release mechanism 22 that is movable between a preparation holding state, as shown in FIG. 3A, for holding the one or more medicine items M in the plurality of preparation compartments 21 and a preparation release state, as shown in FIG. 3B, for releasing the one or more medicine items M from the plurality of preparation compartments 21 in the drop direction D.

In this exemplary embodiment, the preparation release mechanism 22 comprises a preparation release gate or a preparation release plate 23 that is slidable relative to the preparation body 20 in a sliding direction S parallel or substantially parallel to the transport plate plane P. In this exemplary embodiment, the sliding direction S is parallel or substantially parallel to the docking direction A. The preparation release plate 23 is provided with a plurality of preparation release openings 24 which are arranged in the same pattern as the preparation compartments 21. The preparation release plate 23 is movable in the sliding direction S between a preparation holding position, as shown in FIG. 3A, in which the plurality of preparation release openings 24 are out of line with the plurality of preparation compartments 21 and a preparation release position in which the plurality of preparation release openings 24 are registered or aligned with the plurality of preparation compartments 21 in the drop direction D, as shown in FIG. 3B. As all of the preparation release openings 24 are part of the same preparation release plate 23, the one or more medicine items M are released from all preparation compartments 21 of the plurality of preparation compartments 21 simultaneously.

Figure 12:
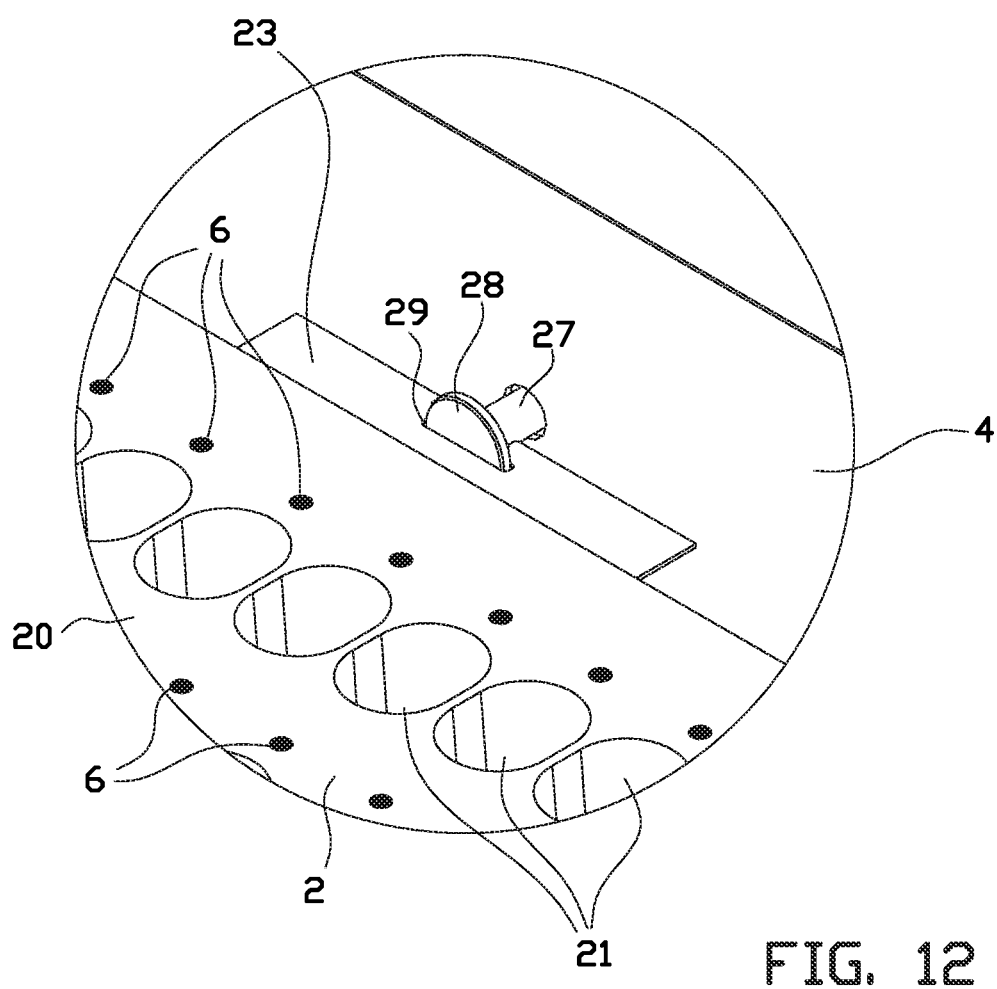
FIG. 12 shows a detail of the docking station according to the circle XII in FIG. 1.

The docking station 1 further comprises a preparation release actuator 25 for driving the movement of the preparation release mechanism 22 between the preparation holding state, as shown FIG. 3A, and the preparation release state, as shown in FIG. 3B. In this exemplary embodiment, the preparation release actuator 25 comprises an electric motor and a plunger-like rod 27 driven linearly in the sliding direction S. As shown in the detail of FIG. 12, the rod 27 is provided with a T-shaped distal end 28 that fits and/or engages with a complementary T-shaped slot 29 in the preparation release plate 23 to drive said preparation release plate 23 in the sliding direction S.

As shown in FIGS. 3A and 3B, the docking station I of the exemplary first embodiment comprises a base 10 for supporting the preparation body 20 in a stacking direction V perpendicular to the transport plate plane P. The docking station 1 is provided with one or more positioning members II for positioning the preparation body 20 on the base 10 in a direction parallel to the transport plate plane P. In this exemplary embodiment, the positioning members 11 are formed like pins that project in an upright orientation from the base 10. The preparation body 20 is provided with corresponding holes to slide said preparation body 20 in the stacking direction V over said positioning members 11. As such, the preparation body 20 is easily removable from the base 10 in the stacking direction V, i.e. for cleaning purposes or for exchange with another preparation body 20 with a different arrangement or pattern of the storage compartments compatible with a different type of medicine transport plate (not shown). The docking station 1 may be provided with a detection element (not shown), i.e. a sensor or the like, may be provided to detect the correct re-assembly or replacement of the preparation body 20, the preparation release plate 23 and/or other parts required for the operation of the docking station 1. When one or more of said parts appear to be missing, the loading process can be interrupted or may not start at all.

The base 10 is provided with a plurality of base chutes or base openings 12 to guide the medicine items M released from the preparation section 2 into the medicine transport plate 9 below, as shown in FIG. 3B.

As further shown in FIG. 3B, the transport plate section 4 comprises a holder or a housing 40 for holding the medicine transport plate 9 in the transport plane P. In particular, the transport plate section 4 comprises a housing 40 that defines a slot 42 extending in the transport plate plane P for holding the medicine transport plate 9 in said transport plate plane P within the housing 40. The slot 42 is open in a docking direction A parallel to the transport plate plane P for slidably receiving the medicine transport plate 9 into said slot 42. The housing 40 is further provided with a transfer opening 41 above the transport plate plane P to allow transfer of the medicine items M released from the preparation section 2 in the drop direction D into the medicine transport plate 9 within said housing 40.

Figure 7:
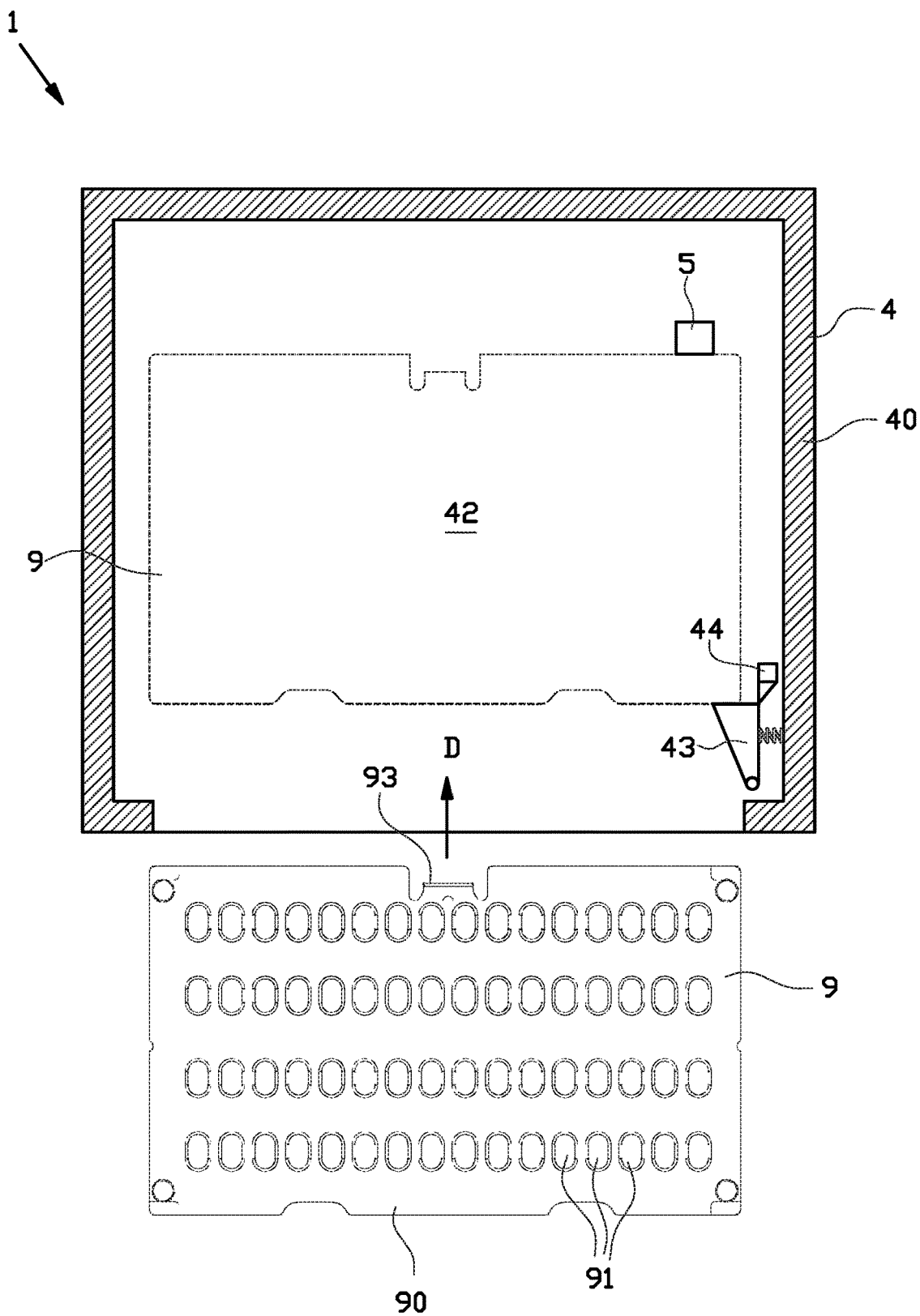
FIG. 7 shows a cross section of the docking station medicine transport plate according to the line VII-VII in FIG. 1 during its interaction with the medicine transport plate.

As shown in FIG. 7, the transport plate section 4 further comprises a transport plate locking member 43 for locking the medicine transport plate 9 in the slot 42 when the medicine transport plate 9 is correctly received in said slot 42. In this exemplary embodiment, the transport plate locking member 43 comprises a wedge-shaped element that is biased by a spring to move into the position as shown in FIG. 7 behind the correctly positioned medicine transport plate 9 (shown in dashed lines) as soon as the medicine transport plate 9 passes the transport plate locking member 43 in the docking direction A.

Optionally, the transport plate section 4 further comprises a transport plate blocking member 44 for preventing insertion of the medicine transport plate 9 into the slot 42. In this exemplary embodiment, the transport plate blocking member 44 cooperates with the transport plate locking member 43 to block the insertion of the medicine transport plate 9 into the slot 42. In particular, the transport plate blocking member 44 may block the movement of the transport plate locking member 43 such that the transport plate locking member 43 is in the path of the medicine transport plate 9 in the docking direction A. The transport plate blocking member 44 may for example be a solenoid that is arranged to engage the transport plate locking member 43 and fixate said transport plate locking member 43 in the position as shown in FIG. 7.

FIGS. 8A, 8B, 9 and 10 show further alternative docking stations 301, 401, 501 with alternative transport plate locking members 343, 443, 543 for locking and/or blocking the medicine transport plate 9.

Figure 8A:
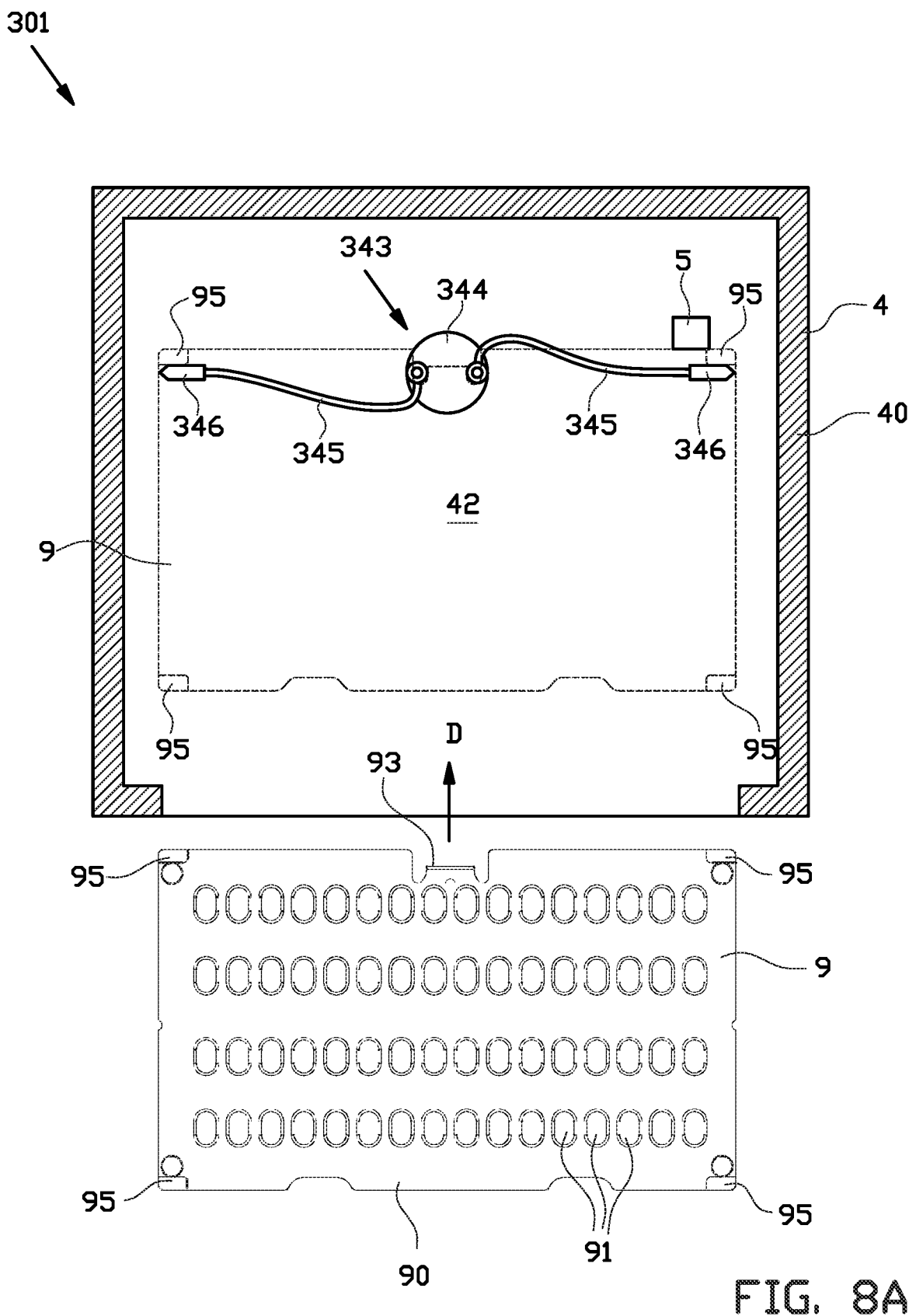
FIGS. 8A and 8B show an alternative docking station.
Figure 8B:
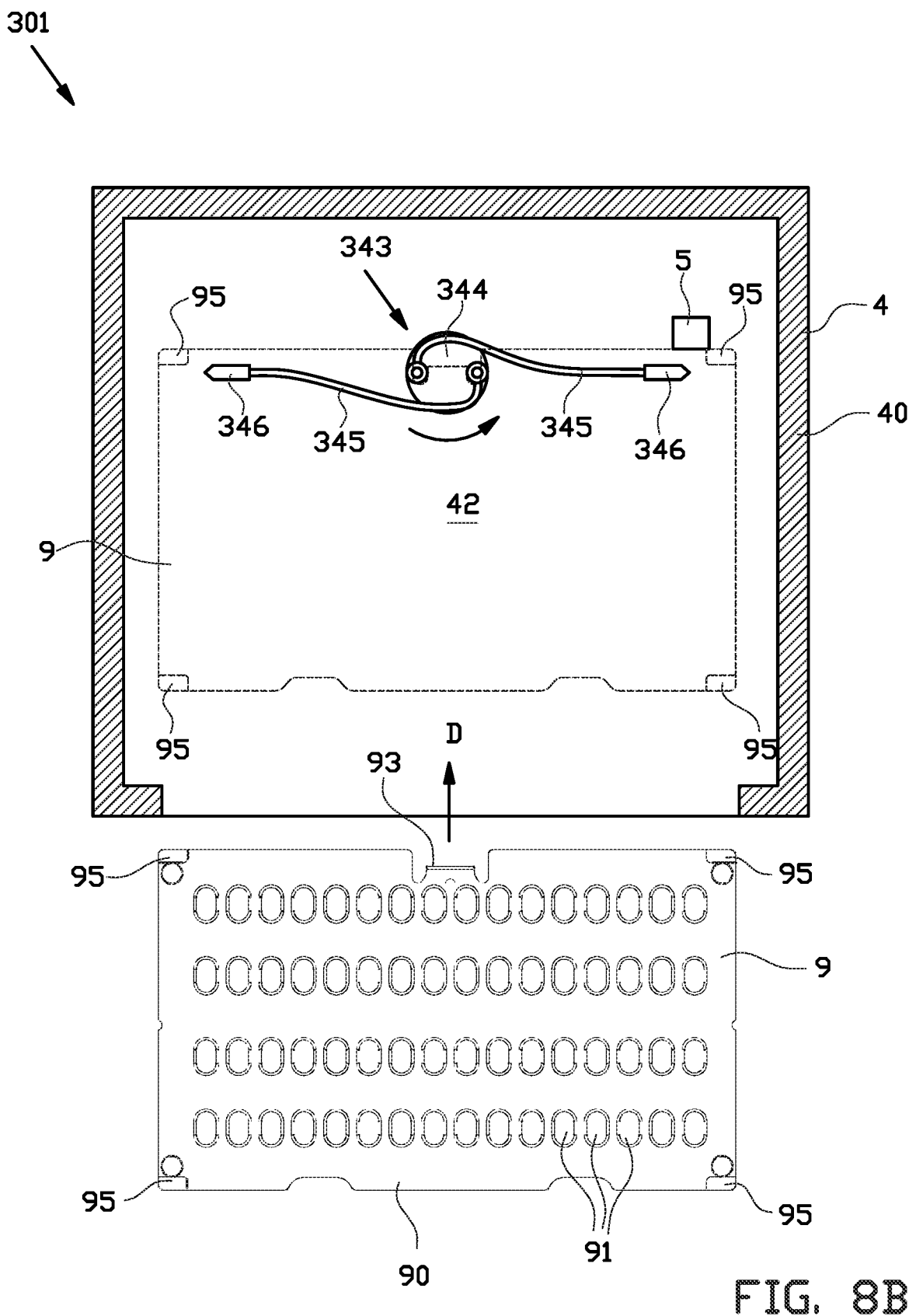

In particular, FIGS. 8A and 8B show an alternative docking station 301 that differs from the previously discussed docking station 1 in that the transport plate locking member 343 comprises two locking pins 346 that are driven in sideways or lateral motion into a position behind the transport plate feet 95, as shown in FIG. 8A, and can be retracted inwards into the position as shown in FIG. 8B to release the medicine transport plate 9. In this example, the locking pins 346 are driven laterally by a central rotary motor 344 and two locking arms 345 that connect the motor 344 to the locking pins 346. Other driving mechanisms can be envisioned to obtain the same lateral locking motion.

Figure 9:
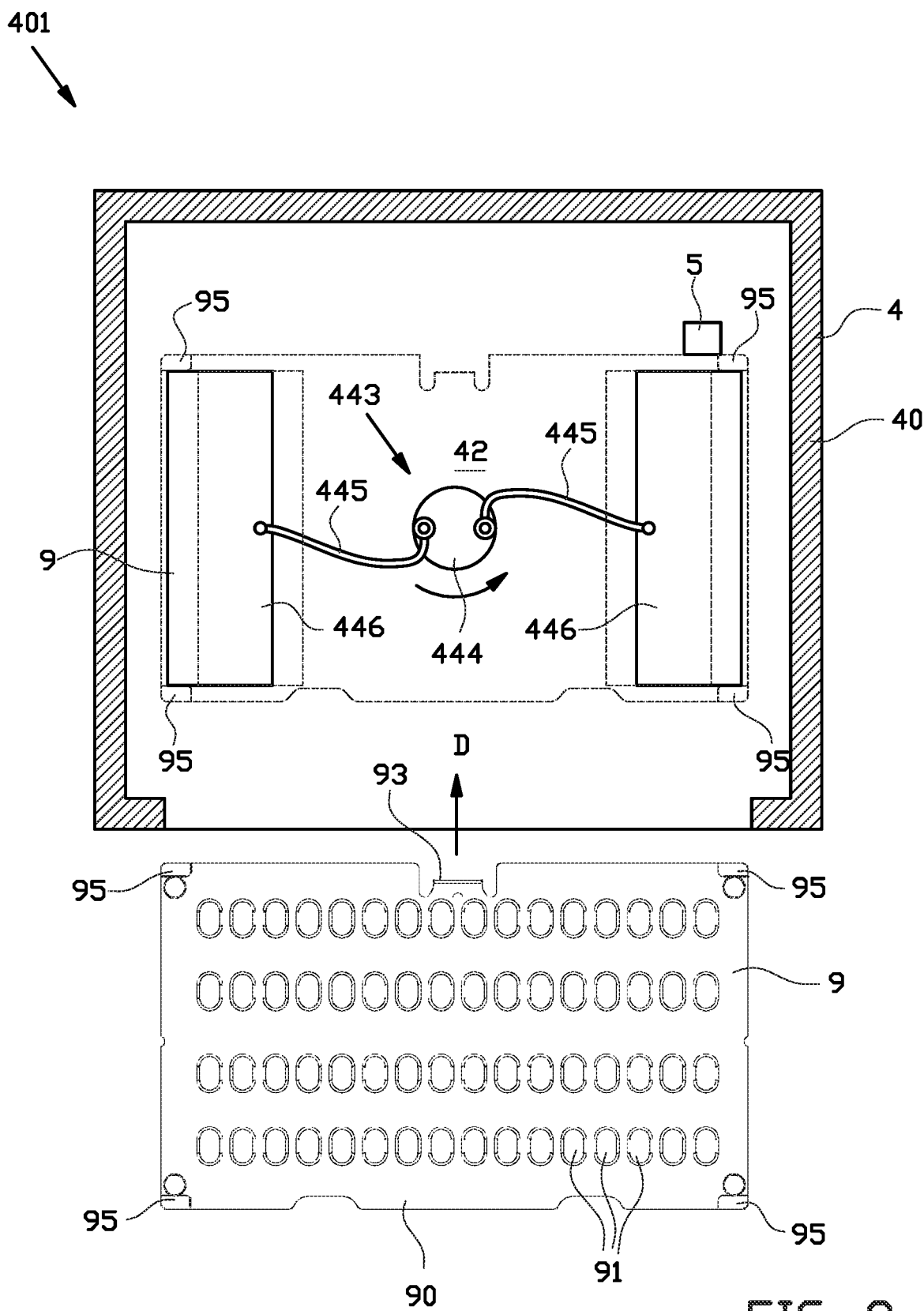
FIG. 9 shows a cross section of a further alternative docking station according to a fourth exemplary embodiment of the invention interacting with the medicine transport plate.

FIG. 9 shows a further alternative docking station 401 that operates in essentially the same way as the docking station 301 shown in FIGS. 8A and 8B in that is has a transport plate locking member 443 that locks the medicine transport plate 9 in place through a sideways or lateral motion. The further alternative docking station 401 differs from the docking station 301 as shown in FIGS. 8A and 8B in that its transport plate locking member 443 comprises two locking blocks 446 which are driven by locking arms 445 driven by a rotary motor 444 similar to the rotary motor 344 of FIGS. 8A and 8B.

Figure 10:
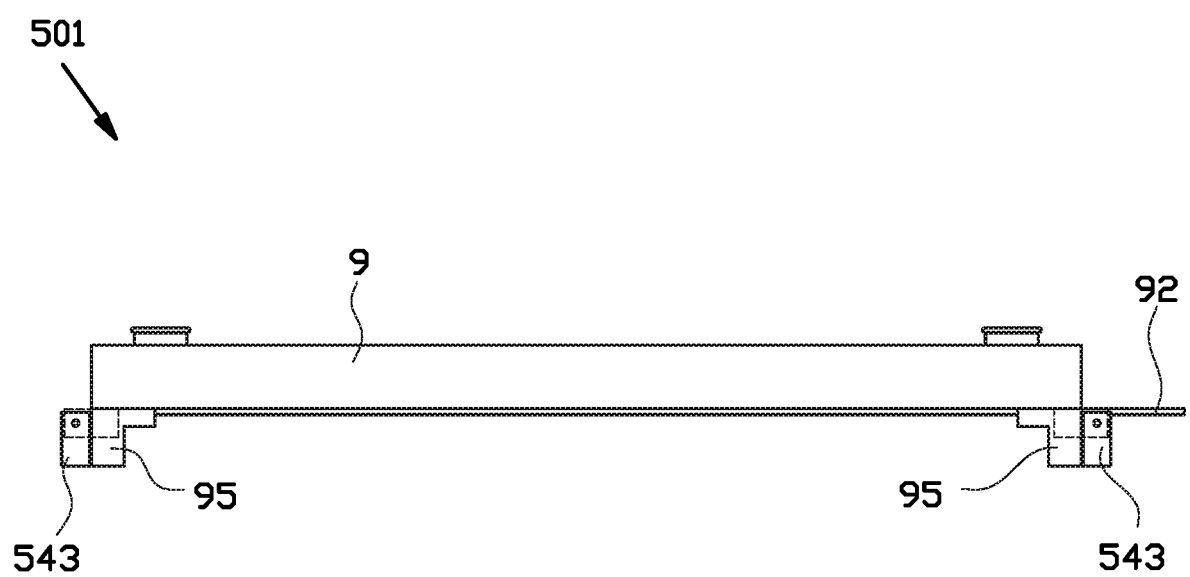
FIG. 10 shows a frontal cross section of a further alternative docking station according to a fifth exemplary embodiment of the invention interacting with the medicine transport plate.

FIG. 10 shows a further alternative docking station 501 with two transport plate locking members 543 that swivel into the space underneath the medicine transport plate 9, i.e. between the transport plate feet 95, as shown in dashed lines.

It will be appreciated by one skilled in the art that many further variations are possible to obtain the locking and/or the blocking functionality as described above, i.e. by hooking onto, engaging with and/or interacting with the medicine transport plate 9, i.e. with a hook, a biased plate, a sliding gate, etc. The locking and/or blocking functionality may be obtained by moving corresponding locking and/or blocking members in different directions or planes than the ones as shown. Moreover, alternative actuation mechanisms can be envisioned, including—but not limited to; driving the locking and/or blocking members directly, indirectly, through a transmission, a gear rack, a piston or the like.

As best shown in FIG. 7, the docking station 1 comprises a sensor 5 for detecting presence or absence of the medicine transport plate 9 in the transport plate section 4. Suitable types of sensors could include, but are not limited to: optical sensors, proximity sensors, laser sensors, light sensors, touch sensors, etc. Optionally, multiple sensors may be provided, i.e. to detect the entry or passage of the medicine transport plate 9 through the slot 42 and/or to detect the arrival of the medicine transport plate 9 in the correct position within the slot 42. Preferably, the preparation release mechanism 22 is arranged to operate automatically in response to the insertion of the medicine transport plate 9 in the slot 42, i.e. upon detection by said one or more sensors 5.

As shown in FIG. 1, the docking station 1 further comprises a plurality of controllable indicators 6 for selectively indicating one or more preparation compartments 21 of the plurality of preparation compartments 21. In particular, one indicator 6 is provided next to or near one preparation compartment 21 of the plurality of preparation compartments 21. In this exemplary embodiment, the plurality of indicators 6 are visual indicators. The indicators 6 may thus conveniently visually indicate which of the preparation compartments 21 are ready to receive a medicine item of a certain type, i.e. with an 'on' or 'off' light. The indicators 6 may further shown different colour codes or patterns to indicate the number or type of medicine items M to be inserted.

The indicators 6 are viewable at or near the preparation compartments 21, in particular at or near the top surface of the preparation body 20. In this exemplary embodiment, the indicators 6 are LED's provided or mounted in the preparation body 20. The preparation body 20 may be provided with an electronic connector (not shown) for connection to and/or communication with the control unit 7.

As shown in FIGS. 1, 3A and 3B, the docking station 1 further comprises a control unit 7 that is operationally and/or electronically connected to the one or more sensors 5, the preparation release actuator 25 and/or the plurality of indicators 6. The control unit 7 is adapted, arranged, programmed and/or configured for controlling the preparation release actuator 25 to maintain the preparation release mechanism 22 in the preparation holding state, as shown in FIG. 3A, as long as the control unit 7 receives a signal from the one or more sensors 5 indicative of the absence of the medicine transport plate 9 in or from the transport plate section 4. It is noted that a 'signal indicative of the absence of the medicine transport plate' in this embodiments and any embodiments described hereafter can be an electronic signal or the absence of such an electronic signal from the one or more sensors 5, depending on how the control unit 7 is configured to interpret the electronic signals, or absence thereof, from the one or more sensors 5. In other words, in absence of the medicine transport plate 9, the one or more sensors 5 can emit a digital 'zero' signal or no electronic signal at all. When the medicine transport plate 9 is detected, the one or more sensors 5 can emit a digital 'one' signal or another suitable electronic signal representative of the presence of the medicine transport plate 9 in the slot 42.

The control unit 7 may further be adapted, arranged, programmed and/or configured for disabling the plurality of indicators 6 when the control unit 7 receives a signal from the one or more sensors 5 indicative of the presence of the medicine transport plate 9 in or from the transport plate section 4.

Hence, the preparation of the one or more medicine items M can only be performed with the aid of the plurality of indicators 6 when the medicine transport plate 9 is not present in the transport plate section 4, corresponding to the situation as shown in FIG. 3A. This forces the operator to first complete the manual preparation of the one or more medicine items M in the preparation section 2 prior to insertion of the medicine transport plate 9 in the transport plate section 4. Moreover, the preparation release mechanism 22 can only be moved into the release position as shown in FIG. 3B when the medicine transport plate 9 is present in the transport plate section 4, to prevent a release of the medicine items M into the transport plate section 4 when the medicine transport plate 9 is absent.

As shown in FIG. 1, the docking station 1 according to the first exemplary embodiment of the invention further comprises a scanner 8 for verification purposes. The docking station 1 may further comprise a user interface (not shown) that is either integrated with the housing of the docking station 1 or externally connected to the electronics of the docking station 1, i.e. as a remote computer.

FIGS. 2 and 4A-4C show an alternative docking station 101 according to an exemplary second embodiment of the invention that differs from the previously described docking station 1 in that it further comprises a buffer section 103 in the drop direction D between the preparation section 2 and the transport plate section 4. The buffer section 103 comprises a plate-like buffer body 130 and a plurality of buffer cells or buffer compartments 131 extending in the drop direction D through said buffer body 130 for receiving the one or more medicine items M from the preparation section 2 prior to loading the medicine transport plate 9. The buffer compartments 131 are arranged in the same pattern as the preparation compartments 21 and, as such, are aligned with or form a continuation of said preparation compartments 21 in the drop direction D. The buffer section 103 further comprises a buffer release mechanism 132 that is movable between a buffer holding state, as shown in FIGS. 4A and 4B, for holding the one or more medicine items M in the plurality of buffer compartments 131 and a buffer release state, as shown in FIG. 4C, for releasing the one or more medicine items M from the plurality of buffer compartments 131 in the drop direction D.

In this exemplary embodiment, the buffer release mechanism 132 essentially operates in the same way or substantially the same way as the preparation release mechanism 22. In particular, the buffer release mechanism 132 comprises a buffer release plate 133 with a plurality of buffer release openings 134 similar to the buffer release plate 23 of the preparation section 2. The buffer release mechanism 132 can be driven by a buffer release actuator 135 in the same as the preparation release actuator 25 drives the preparation release mechanism 22. The buffer release actuator 135 can be controlled individually from the preparation release actuator 25.

Consequently, the one or more medicine items M can be prepared in the preparation section 2 in several batches, as shown in FIG. 4A. Each batch can be released from the preparation compartments 21 into the buffer compartments 131 located below said preparation compartments 21 in the drop direction D, as shown in FIG. 4B, prior to preparing the next batch. The one or more medicine items M are collected and/or buffered in the buffer compartments 131 until all medicine items M from all of the batches have been prepared and buffered in the buffer compartments 131. The buffer release mechanism 132 can subsequently be moved into the buffer release state, as shown in FIG. 4C, to release all medicine items M collected in one or more of the buffer compartments 131.

The buffer release mechanism 132 can take over the holding functionality from the preparation release mechanism 22 in the same way as previously described for said preparation release mechanism. Hence, the preparation release mechanism 22 can be operated independently of the buffer release mechanism 132 to transfer one or more batches of medicine items M from the preparation section 2 into the buffer section 103, while the buffer section 103 buffers said transferred batches of medicine items M until the medicine transport plate 9 is present in the transport plate section 4. In other words, with the provision of the buffer section 103, the preparation release mechanism 22 can be operated independently of the presence or absence of the medicine transport plate 9 in or from the transport plate section 4.

The buffer body 130 can be stacked on top of the base 10 in the stacking direction V in the same way as the preparation body 20, i.e. by sliding said buffer body 130 in the stacking direction V over said positioning members 11. In this way, both the preparation body 20 and the buffer body 130 can be removed from the alternative docking station 101 for cleaning purposes or for switching over to a different configuration of the medicine transport plate.

As best seen in FIGS. 4A-4C, the plurality of preparation compartments 21 are wider than the plurality of buffer compartments 131 in at least one direction perpendicular to the drop direction D, in particular near the top of the preparation body 20. Hence, the medicine items M can remain easily visible in the preparation compartments 21, i.e. near the upper surface of the alternative docking station 101, until they are released through the preparation release mechanism 22 into the buffer section 103 below.

The alternative docking station 101 comprises a user interface that is integrated with the housing of the docking station 1, i.e. a display or touch screen 180 for user input and/or guidance during the loading or filling process. Alternatively, the user interface may comprise one or more physical input elements, such as buttons, knobs or switches. The alternative docking station 101 further comprises a camera 181 to monitor the medicine items M that are placed in the preparation compartments 21 in a manner known per se. The preparation release mechanism 122 may be arranged to be operated semi-automatically via said user-interface 180. The user-interface 180 may be coupled to the control unit 7 or the one or more sensors 5 to disable initiation of the release of the medicine items M from the preparation section 2 and/or the buffer section 103 when certain conditions are not met. In particular, the user-interface may only allow for initiation of the operation of the preparation release mechanism 122 when one or more predetermined checks have been completed, such as the detection of the presence of the medicine transport plate 9 in the slot 42 and/or the identification of the inserted medicine transport plate 9 as the correct medicine transport plate 9 to receive the prepared medicine items M.

Figure 6:
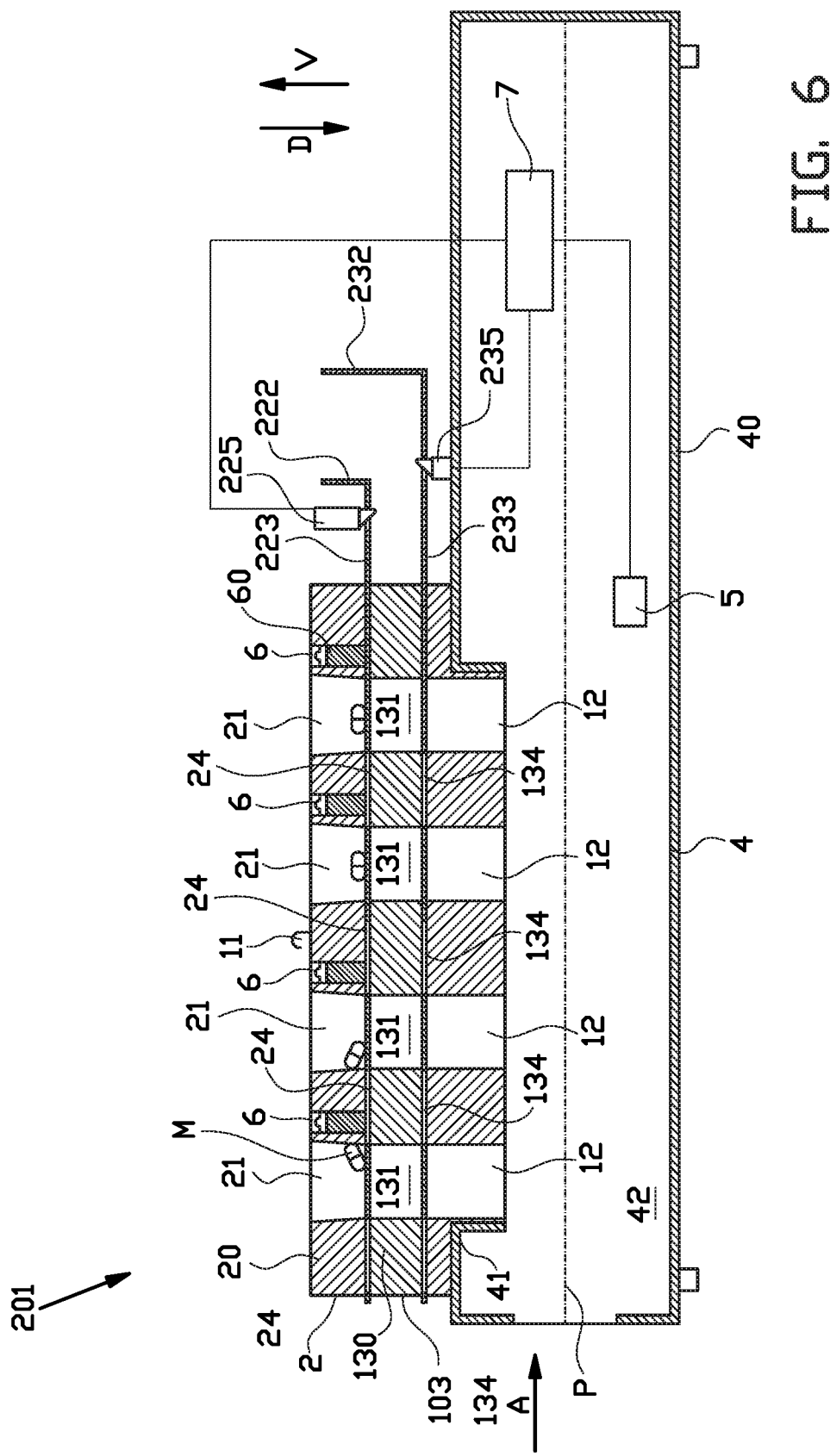
FIG. 6 shows a cross section of a further alternative docking station according to a third exemplary embodiment of the invention.

FIG. 6 shows a further alternative docking station 201 according to an exemplary third embodiment of the invention. The further alternative docking station 201 differs from the previously described docking stations 1, 101 in that its preparation release mechanism 222 and buffer release mechanism 232 can be manually operated. In particular, the preparation release plate 223 and buffer release plate 233 are provided with a handle or a grip to facilitate said manual operation, i.e. manual sliding of said plates 223, 233 in the sliding direction S. Consequently, the further alternative docking station 201 does not feature a preparation release actuator and a buffer release actuator. To prevent manual operation of the preparation release mechanism 222 and the buffer release mechanism 232 when the medicine transport plate 9 is absent in or from the transport plate section 4, the further alternative docking station 201 comprises a preparation blocking member 225 and a buffer blocking member 235 for blocking the movement of the preparation release mechanism 222 and the buffer release mechanism 232, respectively, from their respective holding states to their respective release states. The control unit 7 is again operationally connected to the one or more sensors 5, the preparation blocking member 225 and the buffer blocking member 235, and is adapted, arranged, programmed and/or configured to operate the blocking members 225, 235 in the same way as the actuators 25, 135 of the previously described embodiments of the invention.

Figure 11:
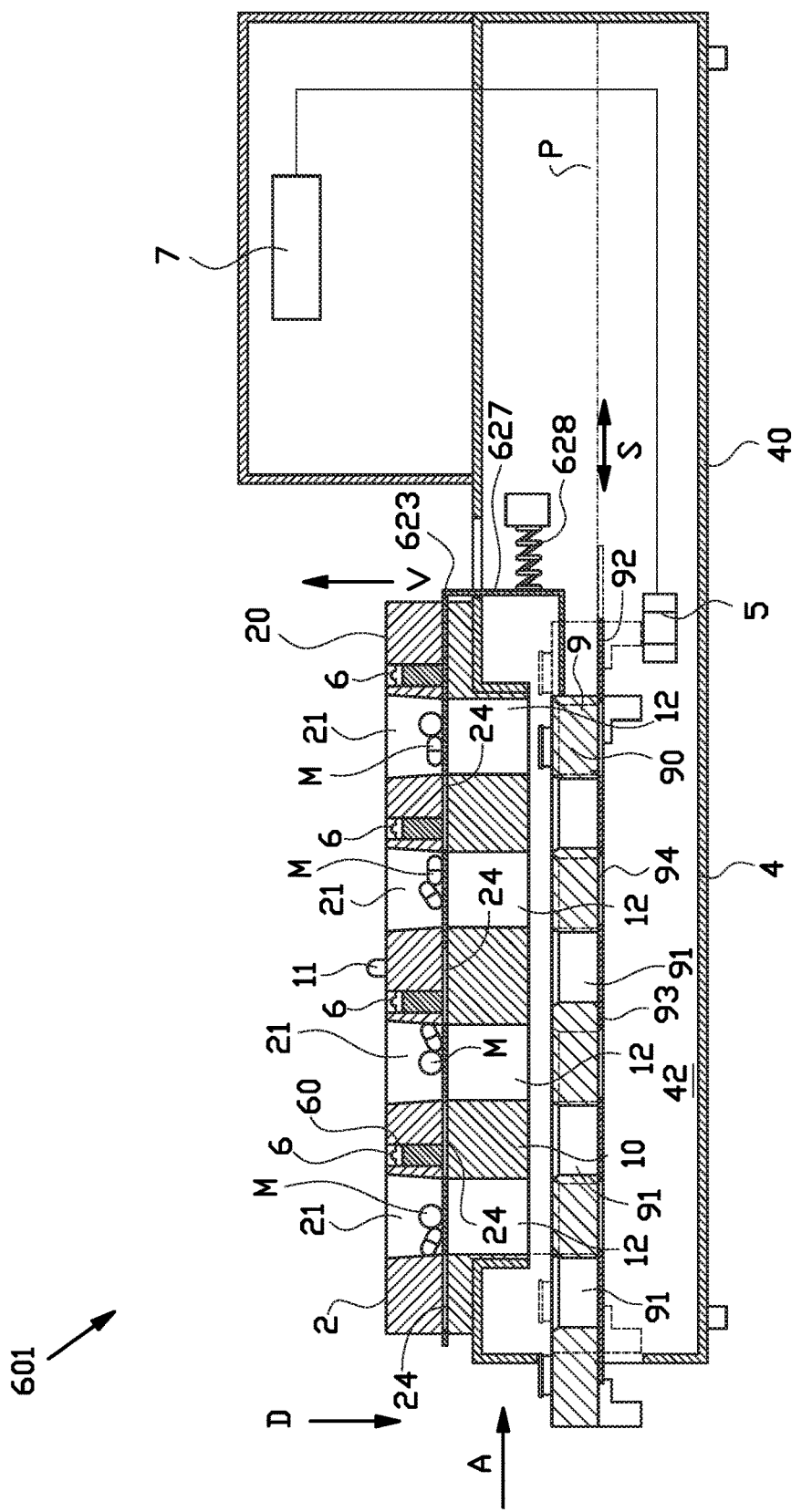
FIG. 11 shows a cross section of a further alternative docking station according to a fifth exemplary embodiment of the invention interacting with the medicine transport plate.

FIG. 11 shows a further alternative docking station 601 that differs from the previously discussed docking stations 1, 101, 201, 301, 401, 501 in that the preparation release plate 623 can be moved automatically from the preparation holding state towards the preparation release state as a result of the insertion of the medicine transport plate 9 into the slot 42 in the docking direction A. In particular, the preparation release plate 623 is provided with a contact member 627 that is arranged for mechanical, physical and/or direct contact with the medicine transport plate 9 as soon as it approaches its intended position within the slot 42. When the medicine transport plate 9 is moved further into the slot 42, it displaces the contact member 627, thereby pushing the preparation release plate 623 from the preparation holding state towards the preparation release state. A biasing member 628, i.e. a spring, is provided to bias or urge the preparation release plate 623 back into the preparation holding state when the medicine transport plate 9 is removed from the slot 42.

The steps of the method for filling or loading the medicine transport plate 9 with the use of any one of the aforementioned docking stations 1, 101, 201 can be derived from the drawings and from the operation of said docking stations 1, 101, 201 which has been described extensively in the foregoing description and will not be described in detail hereafter.

In one particular embodiment of the invention, the control unit 7 may be configured, programmed, adapted and/or arranged to provide an 'abort' or 'discard' functionality, i.e. a button or user-interface element that provides the operator with the option to indicate that loading process is to be aborted, for example because of an error that can not or may not be corrected. Following the activation of this functionality, the control unit 7 is configured to only accept a 'waste' medicine transport plate 9 into the docking station 1, 101, 201, 301, 401, 501, i.e. by first identifying the medicine transport plate 9 based on an information tag, a geometric feature or another distinguishing characteristic. The docking station 1, 101, 201, 301, 401, 501, 601 may for example be configured to read RFID tags. The 'waste' medicine transport plate 9 may be adapted to be incompatibly with or to be rejected by the automated dispensing device to prevent accidental insertion of the 'waste' medicine transport plate 9 in the automated dispensing device.

It is to be understood that the above description is included to illustrate the operation of the embodiments and is not meant to limit the scope of the invention. From the above discussion, many variations will be apparent to one skilled in the art that would yet be encompassed by the scope of the present invention.

LIST OF REFERENCE NUMERALS 1 docking station
10 base
11 positioning member
12 base opening
2 preparation section
20 preparation body
21 preparation compartment
22 preparation release mechanism
23 preparation release plate
24 preparation release opening 25 preparation release actuator
27 rod
28 T-shaped distal end
29 T-shaped slot
4 transport plate section
40 housing
41 transfer opening
42 slot
43 transport plate locking member
44 transport plate blocking member
5 sensor
6 indicator
7 control unit
8 scanner
9 medicine transport plate
90 transport plate body
91 storage compartments
92 transport plate release mechanism
93 transport plate release plate
94 transport plate release openings
95 transport plate foot
101 alternative docking station
103 buffer section
130 buffer body
131 buffer compartment 132 buffer release mechanism
133 buffer release plate
134 buffer release opening
135 buffer release actuator
180 display
181 camera
201 further alternative docking station
202 preparation section
222 preparation release mechanism
223 preparation release plate
225 preparation blocking member
203 buffer section
232 buffer release mechanism
233 buffer release plate
235 buffer blocking member
301 further alternative docking station
343 transport plate locking member
344 locking motor
345 locking arm
346 locking pin
401 further alternative docking station
443 transport plate locking member
444 locking motor
445 locking arm
446 locking block
501 further alternative docking station
543 transport plate locking member
601 further alternative docking station
623 preparation release plate
627 contact member
628 biasing member
A docking direction
D drop direction
M medicine item
P transport plate plane
S sliding direction
V stacking direction

The invention claimed is:

1. A Method for loading a medicine transport plate with one or more medicine items using a docking station, wherein the docking station comprises a preparation section and a buffer section between the preparation section and a transport plate section, the buffer section comprising a plurality of buffer compartments for receiving the one or more medicine items from the preparation section and a buffer release mechanism movable between a buffer holding state and a release state, wherein the method comprises the steps of:
   a) moving a preparation release mechanism of the docking station into a preparation holding state and moving the buffer release mechanism into the buffer holding state;
   b) inserting the one or more medicine items into one or more preparation compartments of a plurality of preparation compartments in the preparation section;
   c) moving the preparation release mechanism from the preparation holding state into a preparation release state to release the one or more medicine items from the preparation compartments;
   d) receiving the one or more medicine items from the preparation section and holding said one or more medicine items in the plurality of buffer compartments;
   e) loading the medicine transport plate into the docking station; and
   f) moving the buffer release mechanism from the buffer holding state into the buffer release state to release the one or more medicine items from the plurality of buffer compartments to the transport plate.

2. The method according to claim 1, wherein the one or more medicine items are released from all preparation compartments of the plurality of preparation compartments simultaneously.

3. The method according to claim 1, wherein the preparation release mechanism is maintained in the preparation holding state as long as the medicine transport plate has not been loaded into the docking station.

4. The method according to claim 1, wherein the preparation release mechanism is operated automatically in response to the loading of the medicine transport plate.

5. The method according to claim 1, wherein the preparation release mechanism is operated semi-automatically via a user-interface.

6. The method according to claim 1, wherein the preparation release mechanism is manually operated.

7. The method according to claim 1, wherein the one or more medicine items are released from all buffer compartments of the plurality of buffer compartments simultaneously.

8. The method according to claim 1, wherein the buffer release mechanism is maintained in the buffer holding state as long as the medicine transport plate has not been loaded into the docking station.

9. The method according to claim 1, wherein the docking station further comprises a plurality of controllable indicators for selectively indicating one or more preparation compartments of the plurality of preparation compartments, wherein the method further comprises the step of disabling the plurality of indicators when the medicine transport plate is present in the transport plate section.

10. The method according to claim 1, wherein the docking station comprises a housing that defines a slot for receiving the medicine transport plate, wherein the method further comprises the step of locking the medicine transport plate in the slot.

11. The method according to claim 1, wherein the method comprises preventing the insertion of the medicine transport plate until the operator first completes manual preparation of the one or more medicine items.

12. The method according to claim 1, wherein the method comprises forcing the operator to first complete manual preparation of the one or more medicine items prior to insertion of the medicine transport plate.

13. The method according to claim 12, wherein the forcing of the operator to first complete manual preparation of the one or more medicine items prior to insertion of the medicine transport plate comprises: using a control unit coupled to a user-interface, and only allowing for the insertion of the medicine transport plate and subsequent release of the one or more medicine items when an operator confirms on the user interface that all of the one or more medicines have been prepared.

14. A docking station for loading a medicine transport plate with one or more medicine items, wherein the medicine transport plate comprises a plurality of storage compartments for receiving the one or more medicine items from the docking station, the docking station comprising:
   a preparation section comprising a plurality of preparation compartments for receiving the one or more medicine items and a preparation release mechanism movable between a preparation holding state and a preparation release state;
   a transport plate section for receiving a medicine transport plate; and a control unit configured to force the operator to first complete preparation of the one or more medicine items in the preparation section prior to insertion of the medicine transport plate in the transport plate section.

15. The docking station of claim 14, and further comprising one or more sensors for detecting presence or absence of the medicine transport plate in the transport plate section, wherein the control unit is further configured to maintain the preparation release mechanism in the preparation holding state as long as the control unit receives a signal from the one or more sensors indicative of the absence of the medicine transport plate in the transport plate section.

16. The docking station of claim 14, and further comprising a plurality of controllable indicators for selectively indicating one or more preparation compartments of the plurality of preparation compartments.

17. The docking station according to claim 14, wherein the preparation release mechanism is manually operable.

18. The docking station according to claim 14, and further comprising a buffer section between the preparation section and the transport plate section, wherein the buffer section comprises a plurality of buffer compartments for receiving the one or more medicine items from the preparation section, and a buffer release mechanism movable between a buffer holding state and a buffer release state.

19. The docking station according to claim 18, wherein the control unit is configured to force the operator to first release the one or more medicine items in the preparation section into the buffer section prior to insertion of the medicine transport plate in the transport plate section.

20. The docking station according to claim 18, wherein the buffer release mechanism comprises a buffer release plate with a plurality of buffer release openings, wherein the buffer release plate is movable in a sliding direction parallel to the transport plate plane between a buffer holding position in which the plurality of buffer release openings are out of line with the plurality of buffer compartments and a buffer release position in which the plurality of buffer release openings are registered with the plurality of buffer compartments.

21. The docking station according to claim 18, wherein the plurality of preparation compartments comprise at least one side wall with a taper such that the opening at a top of the preparation compartment is wider than an opening at the bottom in at least one direction.

22. The docking station according to claim 18, wherein the preparation section and the buffer section comprise a preparation body and a buffer body, respectively, wherein the plurality of preparation compartments and the plurality of buffer compartments are formed in said preparation body and said buffer body, respectively, wherein the docking station further comprises a base for supporting the preparation body and the buffer body in a stacking direction.

23. The docking station of claim 22, wherein the preparation body and the buffer body are removable from the base in the stacking direction.

24. A docking station for loading a medicine transport plate with one or more medicine items, wherein the medicine transport plate comprises a plurality of storage compartments for receiving the one or more medicine items from the docking station, the docking station comprising:
   a preparation section comprising a plurality of preparation compartments for receiving the one or more medicine items and a preparation release mechanism movable between a preparation holding state and a preparation release state;
   a transport plate section for receiving a medicine transport plate; and
   a control unit configured to prevent the insertion of the medicine transport plate until the operator first completes manual preparation of the one or more medicine items.

25. The docking station of claim 24, and further comprising one or more sensors.

26. The docking station of claim 24, and further comprising a buffer section between the preparation section and the transport plate section, wherein the control unit is configured to prevent the insertion of the medicine transport plate until the operator first completes preparation of the one or more medicine items, and the one or more medicine items have been released from the preparation section to the buffer section.

* * * * *